United States Patent
Ntana et al.

(10) Patent No.: US 12,415,997 B2
(45) Date of Patent: Sep. 16, 2025

(54) **METHOD FOR PRODUCING THE SESQUITERPENE VIRIDIFLOROL WITH A FU

METHOD FOR PRODUCING THE SESQUITERPENE VIRIDIFLOROL WITH A FUNGAL ENZYME

This application is U.S. National Stage Filing under 35 U.S.C. 371 of International Patent Application Serial No. PCT/US2020/050354, filed Sep. 11, 2020, and published as WO 2021/050841 A2 on Mar. 18, 2021, which claims benefit of priority to the filing date of U.S. Provisional Application Ser. No. 62/899,391, filed Sep. 12, 2019, the contents of which are specifically incorporated herein by reference in their entirety.

BACKGROUND

Fungi may be source of bioactive and structurally diverse terpenoids. However, little is known about the genes responsible for the construction of these unique fungal terpenoid structures.

SUMMARY

As described herein, the basidiomycete *Serendipita indica*, a non-specific-host root endophyte fungus, possesses a functional terpenoid synthase gene (SiTPS).

Heterologous expression of SiTPS in host cells showed that the produced protein efficiently utilizes the fifteen-carbon precursor farnesylpyrophosphate (FPP) to synthesize the sesquiterpene alcohol viridiflorol, shown below.

Viridifloral

Viridiflorol has a highly characteristic scent and has utility in the perfume industry. It is also useful as bioactive molecule, with antibacterial, anti-inflammatory and antioxidant activities. For example, viridiflorol has antimicrobial activity against tuberculosis or other clinically relevant strains of multi-drug resistant (MDR) bacteria. Viridiflorol is found in essential oils of a variety of plants including *Melaleuca quinquenervia* (broad-leaved paperbark), *Melaleuca alternifolia* (tea tree), and *Allophylus edulis*. This is the first report of a SiTPS gene encoding a viridiflorol synthase.

Described herein are expression cassettes that include a heterologous promoter operably linked to a nucleic acid segment encoding a *Serendipita indica* terpenoid synthase (SiTPS), where the *Serendipita indica* terpenoid synthase can synthesize viridiflorol.

Described herein are host cells that have one or more are expression cassettes that include a heterologous promoter operably linked to a nucleic acid segment encoding a *Serendipita indica* terpenoid synthase (SiTPS), where the *Serendipita indica* terpenoid synthase can synthesize viridiflorol.

Also described herein are fungi, spores, plants and seeds that have one or more expression cassettes, each expression cassette having a heterologous promoter operably linked to a nucleic acid segment encoding a *Serendipita indica* terpenoid synthase (SiTPS), where the *Serendipita indica* terpenoid synthase can synthesize viridiflorol.

Also described herein are methods for synthesizing viridiflorol that include incubating one or more host cells that have one or more expression cassettes, each expression cassette having a heterologous promoter operably linked to a nucleic acid segment encoding a *Serendipita indica* terpenoid synthase (SiTPS), where the *Serendipita indica* terpenoid synthase can synthesize viridiflorol.

Also described herein are methods for synthesizing viridiflorol that include cultivating one or more seeds that have one or more expression cassettes, each expression cassette having a heterologous promoter operably linked to a nucleic acid segment encoding a *Serendipita indica* terpenoid synthase (SiTPS), where the *Serendipita indica* terpenoid synthase can synthesize viridiflorol.

DESCRIPTION OF THE FIGURES

FIG. 1A-1B illustrate several biosynthetic pathways of sesquiterpenoids. FIG. 1A-1 to 1A-4 show biosynthetic pathways of several sesquiterpenoids found in Basidiomycota fungi. FIG. 1A-1 illustrates biosynthesis of E,E-FPP and (3R)-NPP. Sesquiterpenoid scaffolds can be distinguished by the first cyclization step of E,E-FPP or (3R)-NPP. Four distinct structural groups can be made. FIG. 1A-2 illustrates biosynthesis of terpenoids derived from 1,10 closure of E,E-FPP (STS Clade 1), and 1,11 closure of E,E-FPP shown in blue (STS Clade III). FIG. 1A-3 illustrates biosynthesis of terpenoids derived from 1,6 or 17 closure of (3R)-NPP (STS Clade IV). FIG. 1A-4 illustrates biosynthesis of terpenoids derived from 1,10 closure of (3R)-NPP shown in blue (STS Clade II) (see also, Wawrzyn et al., 2012b). FIG. 1B-1 to 1B-4 illustrate a biosynthetic pathway leading to the production of viridiflorol and ledol. FIG. 1B-1 shows that viridiflorol biosynthesis can start with 1,10-closure of either NPP (route a-Clade 11) or FPP (route b-Clade I) to form a germacradienyl cation (Z,E or EE, respectively). FIG. 1B-2 illustrates a 1,3 H-shift (C1 to C11) of the germacradienyl cation. FIG. 1B-3 illustrates two cyclisation events (1,11 and 2,6) of the H-shifted germacradienyl cation in the biosynthetic pathway leading to the production of viridiflorol and ledol. FIG. 1B-4 illustrates addition of a molecule of water to the terpenoid generated as shown in FIG. 1B-3, thereby resulting in formation of viridiflorol and ledol (see also, Hong & Tantillo, 2011).

FIG. 2 illustrates *Serendipita indica* terpenoid synthase (SiTPS) phylogenetic relationships. A Maximum-likelihood tree was constructed (bootstrap of 100) using the proteins from NCBI with the highest similarity to SiTPS amino acid sequence. The scale bar indicates a genetic distance of 0.50 and the bootstrap values are shown below the branches. NCBI accession numbers: CCA72799.1 *Serendipita indica* DSM 11827, KIM31075.1 *Serendipita vermifera* MAFF 305830, K1032332.1 *Tulasnella calospora* MUT 4182, AUW30846.1 *Cladonia uncialis* subsp *uncialis*, KDQ10835.1 *Botryobasidium botryosum*, CEL57650.1 *Rhizoctonia solani* AG-1 IB, CUA75792.1 *Rhizoetonia solani*, XP_007869182.1 *Gloeophyllum trabeum* ATCC 11539, OBZ72577.1 *Grifola frondosa*, WP_073739522.1 *Streptomyces* sp, WP_030800135.1 *Streptomyces albovinaceus*, SCG69967.1 *Micromonospora zamorensis*, SFC79096.1 *Verrucosispora sediminis*, SCG62678.1 *Micromonospora coxensis*, SCL17011.1 *Micromonospora rhizosphaerae*, SBV28600.1 *Micromonospora krabiensis*, WP_007454512.1 *Micromonospora lupine*, SCL47036.1 *Micromonospora yangpuensis*, WP_013730983.1 *Verrucosispora maris*.

FIG. 4 graphically illustrates the relative expression of SITPS when *S. indica* is grown for 14 days on CM agar plates (in CM, lighter bar) compared to expression when *S. indica* fungi is colonizing tomato roots (11 days post inoculation, dpi) (in planta, darker bar). Relative expression in both conditions was normalized using SiGAPDH (GenBank: FJ810523.1) expression levels and calculated with the $2^{-\Delta Ct}$ method (Livak & Schmittgen, 2001; Schmittgen & Livak, 2008). Error bars represent the standard deviation (n=4). Asterisk (*) represents significant difference between the two conditions (t-test in Rstudio, *P-value≤0.05).

DETAILED DESCRIPTION

Figures 1, 1A:
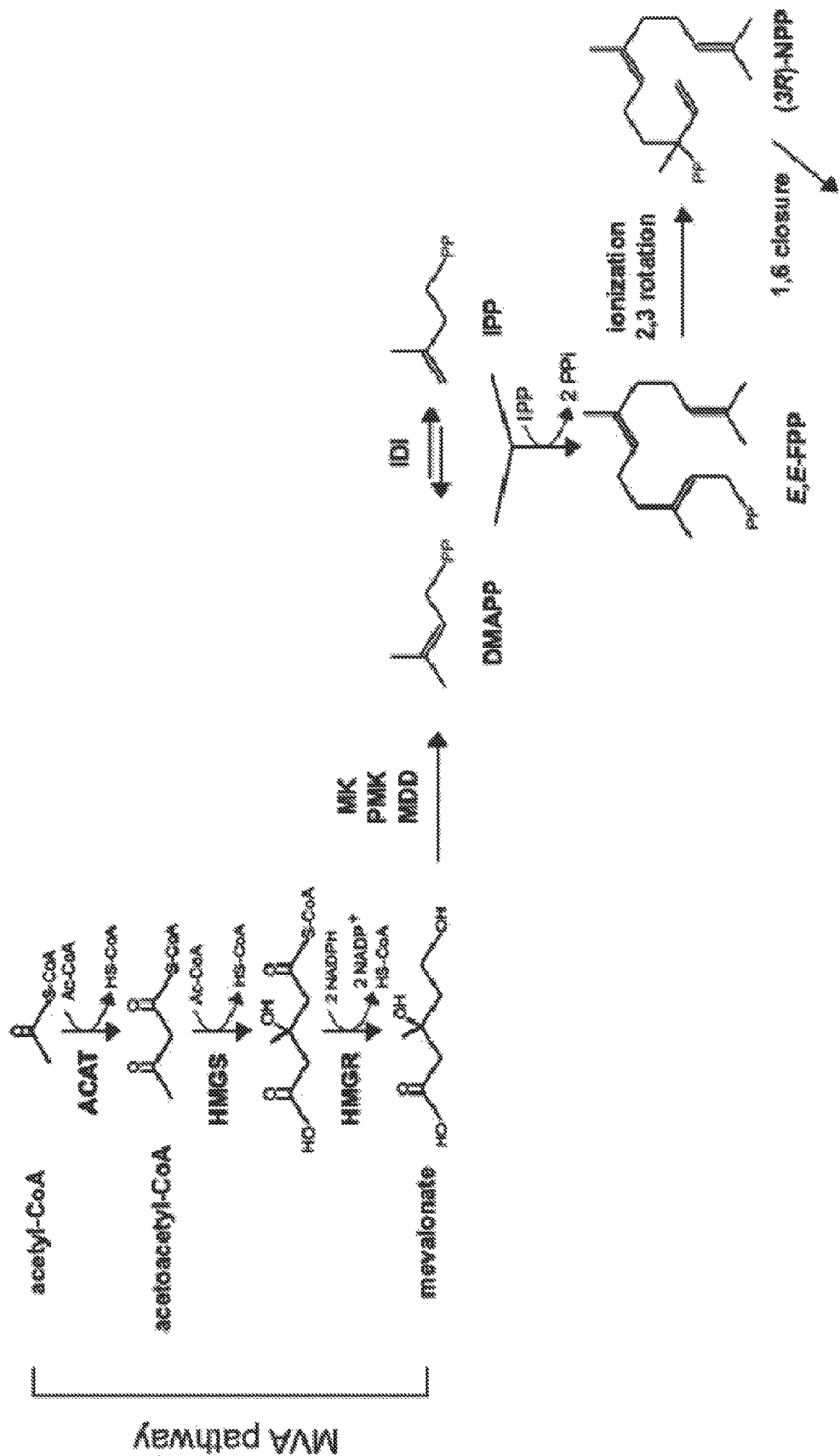

Constructs, host cells, seeds, plants, and methods are described herein that include a *Serendipita indica* terpenoid synthase (SiTPS). Such constructs, host cells, seeds, plants, and methods are useful for making terpenoids such as viridiflorol.

*Serendipita indica* Terpenoid Synthase (SiTPS)

*Serendipita* (also called *Piriformospora*) *indica* is a fungal endophytic symbiont with the capabilities to enhance plant growth and confer resistance to different stresses. However, the application of this fungus in the field has led to inconsistent results. An enzyme from *Serendipita indica* (SiTPS) is described herein that is useful for making terpenoids such as viridiflorol. Volatile terpenoids can mediate communication between plants and microbes and plant terpenoids are involved in the development of ectomycorrhizal associations with several plant species during the pre-symbiotic phase. Despite a couple of attempts (Crutcher et al., 2013), there has previously been no direct evidence that fungal terpenoids could play a role in facilitating establishment of plant-endophytic interactions.

The enzyme from *Serendipita indica* (SiTPS) useful for making terpenoids is referred to as the SiTPS enzyme. This enzyme can have the following amino acid sequence (SEQ ID NO:1).

```
  1   MPSVSPATIR LPDILGAMDR FELRTHPDER EVTRASNEWF
 41   NSYNMMPPAL FEKFVKCDFG LMTGMSYPDT DATRLRITCD
 81   YMSILFAYDD LMDLPSSDLM HDKIASDKAA KIMMGVLTHP
121   HKFRPYAGLP VATAFHDFWT RFCATSTPKM QKRFTDTTYE
161   YVMAVKNQCG NRQSSRCPTI EEYVALRRDT SAIKVTYACI
201   EYCLNIDVPD EAFYHPSVAA LQEAGNNILS WANDVYSFDN
241   EQSSGDCHNL VAIVAINKNI TVQAAMEYVM GMIDSAIERF
281   FEECANVPSF GPEVDPLVQA YIKGVELYLS GSVFWHLESE
321   RYFGARVQHV KDTLMVELRP LDEGAKPAFD LMYKLPSNLT
361   PEVLSAAAVS AAPAAPAPVA SPAPQPEILS PTPISPINVN
401   FPLGNVACPP PSYETQRVLA KMVAATVEEK QRLAYSQPAE
441   QYYSPAPQYY PSQPVEKFQQ TNVLETAFKG SNSELTNILV
481   IASVLMAGSP MALVPFVPLL ALLLLPNETP VAPVAFEHHH
521   HHH
```

A nucleic acid sequence that encodes the SEQ ID NO:1 SiTPS is shown below as SEQ ID NO:2.

```
  1   ATGCCATCTG TCTCTCCTGC CACCATCCGC CTCCCTGATA
 41   TCCTCGGTGC TATGGACCGC TTTGAGCTCC GCACTCACCC
 81   CGATGAGCGC GAAGTCACCC GTGCCTCGAA CGAGTGGTTC
121   AACAGCTACA ACATGATGCC CCCGGCACTC TTTGAAAAGT
161   TTGTCAAGTG CGATTTCGGC CTCATGACCG GCATGTCGTA
201   CCCAGATACC GATGCTACCC GCCTCCGTAT CACTTGCGAC
241   TACATGTCGA TCCTCTTCGC CTATGACGAC CTCATGGACC
281   TCCCCTCGTC CGACCTTATG CATGACAAGA TTGCCTCGGA
321   CAAGGCTGCC AAGATCATGA TGGGTGTCCT CACCCACCCC
361   CACAAGTTCC GCCCATATGC TGGCCTCCCA GTCGCCACTG
401   CTTTCCATGA CTTCTGGACC CGCTTCTGCG CTACTTCGAC
441   CCCAAAGATG CAAAAGCGCT TCACTGACAC CACCTACGAG
481   TATGTCATGG CCGTCAAGAA CCAGTGCGGC AACCGCCAGA
521   GCTCTCGCTG CCCAACCATC GAGGAGTACG TCGCTCTCCG
561   CCGCGACACC TCGGCCATCA AGGTCACCTA TGCTTGCATC
601   GAGTACTGCC TCAACATCGA CGTCCCAGAC GAGGCCTTCT
641   ACCACCCCTC CGTGGCTGCT CTCCAGGAGG CTGGCAATAA
```

```
681  TATCCTCTCG TGGGCCAACG ATGTTTACTC GTTTGACAAC
721  GAGCAATCCT CGGGTGACTG CCACAACCTG GTTGCCATTG
761  TTGCCATCAA CAAGAACATT ACTGTTCAGG CTGCAATGGA
801  GTACGTCATG GGCATGATCG ACTCTGCTAT CGAACGCTTC
841  TTCGAGGAGT GCGCCAACGT CCCTTCGTTC GGCCCCGAAG
881  TCGACCCTCT CGTCCAGGCC TACATCAAGG GTGTCGAGCT
921  CTACCTTAGC GGCTCCGTCT TCTGGCACCT CGAATCCGAG
961  CGCTACTTTG GTGCTCGCGT CCAGCACGTC AAGGATACCT
1001 TGATGGTTGA GCTCCGCCCA CTCGACGAGG GTGCGAAGCC
1041 GGCCTTCGAC CTCATGTACA AGCTCCCATC CAACTTGACG
1081 CCCGAGGTCC TCAGTGCCGC TGCTGTCTCG GCTGCCCCAG
1121 CTGCGCCAGC TCCTGTCGCT CTCCGGCTC CTCAGCCAGA
1161 GATCCTCTCG CCGACGCCAA TCTCGCCCAT CAACGTCAAC
1201 TTCCCTCTCG GCAACGTCGC CTGCCCGCCT CCTTCGTACG
1241 AGACCCAGCG CGTTCTCGCC AAGATGGTGG CCGCGACCGT
1281 CGAGGAGAAG CAGCGCCTTG CTTAGAGCCA GCCAGCTGAG
1321 CAGTACTACT CGCCCGCTCC CCAGTACTAC CCAAGCCAGC
1361 CGGTTGAAAA GTTCCAGCAG ACCAACGTGC TCGAGACCGC
1401 CTTCAAGGGA TCCAACTCGG AATTGACCAA CATTCTCGTT
1441 ATTGCCTCCG TCCTCATGGC CGGATCACCC ATGGCGCTTG
1481 TCCCCTTTGT CCCTCTTCTC GCCCTCCTAC TCCTCCCCAA
1521 CGAGACCCCA GTGGCTCCCG TTGCGTTCGA GCACCACCAC
1561 CACCACCAC
```

The SiTPS enzyme can have one or more amino acids missing from the SEQ ID NO:1 sequence. For example, the SiTPS enzyme can have the C-terminal histidine tag (HHHHHH at positions 518-523) missing. Such a SiTPS enzyme can have the following sequence (SEQ ID NO: 3).

```
1    MPSVSPATIR LPDILGAMDR FELRTHPDER EVTRASNEWF
41   NSYNMMPPAL FEKFVKCDFG LMTGMSYPDT DATRLRITCD
81   YMSILFAYDD LMDLPSSDLM HDKIASDKAA KIMMGVLTHP
121  HKFRPYAGLP VATAFHDFWT RFCATSTPKM QKRFTDTTYE
161  YVMAVKNQCG NRQSSRCPTI EEYVALRRDT SAIKVTYACI
201  EYCLNIDVPD EAFYHPSVAA LQEAGNNILS WANDVYSFDN
241  EQSSGDCHNL VAIVAINKNI TVQAAMEYVM GMIDSAIERF
281  FEECANVPSF GPEVDPLVQA YIKGVELYLS GSVEWHDESE
321  RYFGARVQHV KDTLMVELRP LDEGAKPAFD LMYKLPSNLT
361  PEVLSAAAVS AAPAAPAPVA SPAPQPEILS PTPISPINVN
401  FPLGNVACPP PSYETQRVLA KMVAATVEEK QRLAYSQPAE
441  QYYSPAPQYY PSQPVEKFQQ TNVLETAFKG SNSELTNILV
481  IASVLMAGSP MALVPFVPLL ALLLLPNETP VAPVAFE
```

In another example, the SiTPS enzyme can also have the following amino acid sequence (SEQ ID NO:4), where there is one amino acid missing at about position 218.

```
1    MPSVSPATIR LPDILGAMDR FELRTHPDER EVTRASNEWF
41   NSYNMMPPAL FEKFVKCDFG LMTGMSYPDT DATRLRITCD
81   YMSILFAYDD LMDLPSSDLM HDKIASDKAA KIMMGVLTHP
121  HKFRPYAGLP VATAFHDFWT RFCATSTPKM QKRFTDTTYE
161  YVMAVKNQCG NRQSSRCPTI EEYVALRRDT SAIKVTYACI
201  EYCLNIDVPD EAFYHPSVAA LQEAGNILS  WANDVYSFDN
241  EQSSGDCHNL VAIVAINKNI TVQAAMEYVM GMIDSAIERF
281  FEECANVPSF GPEVDPLVQA YIKGVELYLS GSVFWHLESE
321  RYFGARVQHV KDTLMVELRP LDEGAKPAFD LMYKLPSNLT
361  PEVLSAAAVS AAPAAPAPVA SPAPQPEILS PTPISPINVN
401  FPLGNVACPP PSYETQRVLA KMVAATVEEK QRLAYSQPAE
441  QYYSPAPQYY PSQPVEKFQQ TNVLETAFKG SNSELTNILV
481  IASVLMAGSP MALVPFVPLL ALLLLPNETP VAPVAFEHHH
521  HHH
```

The SiTPS enzyme with SEQ ID NO:4 can also not have the C-terminal histidine tag (HHHHHH, SEQ ID NO:6) at positions 518-523.

Enzymes described herein can have one or more deletions, insertions, replacements, or substitutions in a part of the enzyme. The enzyme(s) described herein can have, for example, at least 60%, or at least 70%, or at least 80%, or at least 90%, or at least 93%, or at least 95%, or at least 96%, or at least 97%, or at least 98%, or at least 99% sequence identity to a sequence described herein.

Nucleic acids encoding one or more enzyme(s) can have one or more nucleotide deletions, insertions, replacements, or substitutions. For example, the nucleic acids encoding one or more enzyme(s) can, for example, have less than 95%, or less than 94.8%, or less than 94.5%, or less than 94%, or less than 93.8%, or less than 94.50% nucleic acid sequence identity to a corresponding parental or wild-type sequence. In some cases, the nucleic acids encoding one or more enzyme(s) can have, for example, at least 50%, or at least 55%, or at least 60%, or at least 65%, or at least 70%, or at least 75%, or at least 80%, or at least 85%, or at 90% sequence identity to a corresponding parental or wild-type sequence.

In some cases, enzymes can have conservative changes such as one or more deletions, insertions, replacements, or substitutions that have no significant effect on the activities of the enzymes. Examples of conservative substitutions are provided below in Table 1A.

TABLE 1A

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulfhydryl | Cys |
| Aliphatic | Val, Ile, Leu, Met |
| Basic | Lys, Arg, His |
| Aromatic | Phe, Tyr, Trp |

Synthetic Pathways

Biosynthetic pathways of several sesquiterpenoids found in Basidiomycota fungi are shown below. For example, the mevalonate (MVA) pathway is shown below (see also FIG. 1A), which provides isopentenyl diphosphate (IPP) and dimethylallyl diphosphate building (DMAPP) building blocks for biosynthesis of isoprenoids.

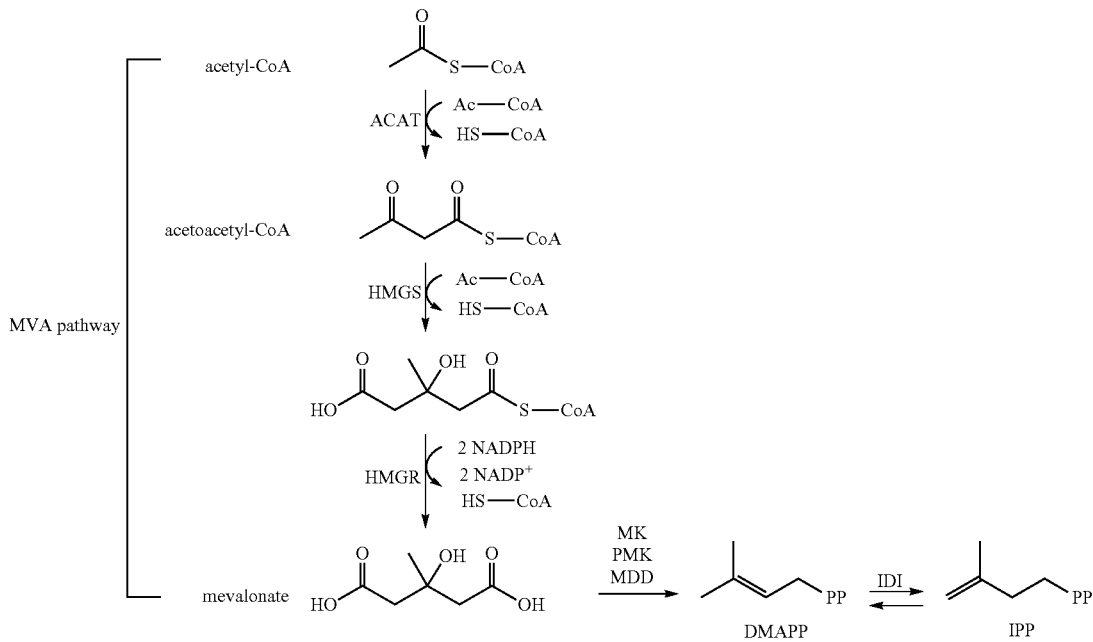

For example, the isopentenyl diphosphate (IPP) and dimethylallyl diphosphate building (DMAPP) are building blocks for E,E-FPP and (3R)-NPP, which are building blocks for synthesis of viridiflorol.

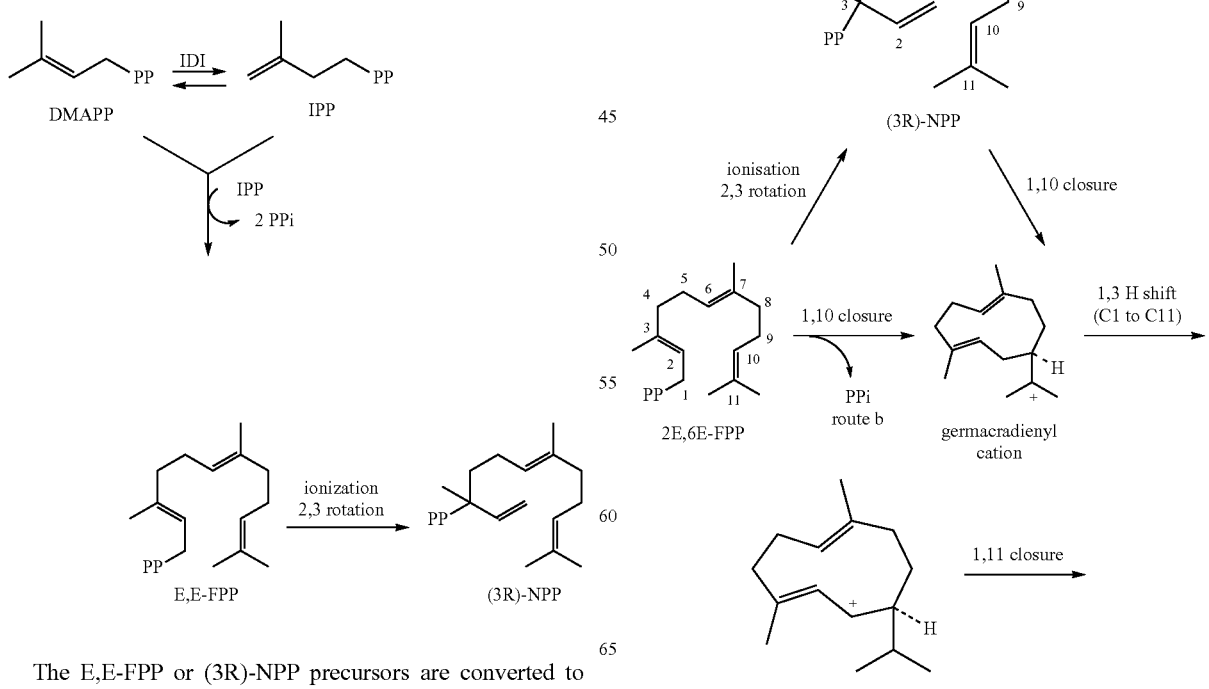

The E,E-FPP or (3R)-NPP precursors are converted to viridiflorol as shown below.

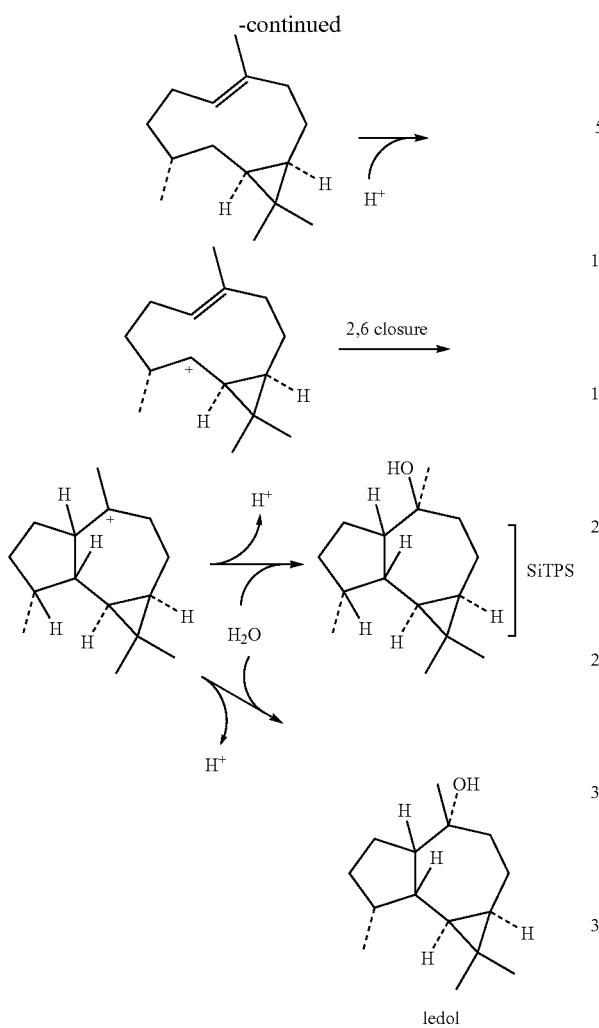

ledol

Viridiflorol biosynthesis starts with a 1,10-closure of either NPP (route a-Clade 11) or FPP (route b-Clade I) to form a germacradienyl cation (Z,E or E,E respectively). Two more cyclisation events (1,11 and 2,6) and the addition of a molecule of water result in the formation of viridiflorol.

Expression of Enzymes

Also described herein are expression systems that include at least one expression cassette (e.g., expression vectors or transgenes) that encode one or more of the enzyme(s) described herein. The expression systems can also include one or more expression cassettes encoding an enzyme that can synthesize terpene building blocks. For example, the expression systems can include one or more expression cassettes encoding terpene synthases that facilitate production of terpene precursors or building blocks such as those involved in the synthesis of isopentenyl diphosphate (IPP) or dimethylallyl diphosphate (DMAPP).

Cells containing such expression systems are further described herein. The cells containing such expression systems can be used to manufacture the enzymes (e.g., for in vitro use) and/or one or more terpenes, diterpenes, sesquiterpenes, or terpenoids produced by the enzymes. Methods of using the enzymes or cells containing expression cassettes encoding such enzymes to make products such as terpenes, diterpenes, terpenoids, and combinations thereof are also described herein.

Nucleic acids encoding the enzymes can have sequence modifications. For example, nucleic acid sequences described herein can be modified to express enzymes that have modifications. Most amino acids can be encoded by more than one codon. When an amino acid is encoded by more than one codon, the codons are referred to as degenerate codons. A listing of degenerate codons is provided in Table 1B below.

TABLE 1B

Degenerate Amino Acid Codons

| Amino Acid | Three Nucleotide Codon |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Different organisms may translate different codons more or less efficiently (e.g., because they have different ratios of tRNAs) than other organisms. Hence, when some amino acids can be encoded by several codons, a nucleic acid segment can be designed to optimize the efficiency of expression of an enzyme by using codons that are preferred by an organism of interest. For example, the nucleotide coding regions of the enzymes described herein can be codon optimized for expression in various plant species. For example, many of the enzymes described herein were originally isolated from the mint family (Lamiaceae), however such enzymes can be expressed in a variety of host cells, including for example, bacterial, fungal, and plant host cells.

An optimized nucleic acid can have less than 98%, less than 97%, less than 95%, or less than 94%, or less than 93%, or less than 92%, or less than 91%, or less than 90%, or less than 89%, or less than 88%, or less than 85%, or less than 83%, or less than 80%, or less than 75% nucleic acid sequence identity to a corresponding non-optimized (e.g., a non-optimized parental or wild type enzyme nucleic acid) sequence.

The enzymes described herein can be expressed from an expression cassette and/or an expression vector. Such an expression cassette can include a nucleic acid segment that encodes an enzyme operably linked to a promoter to drive expression of the enzyme. Convenient vectors, or expression systems can be used to express such enzymes. In some instances, the nucleic acid segment encoding an enzyme is operably linked to a promoter and/or a transcription termination sequence. The promoter and/or the termination sequence can be heterologous to the nucleic acid segment that encodes an enzyme. Expression cassettes can have a promoter operably linked to a heterologous open reading frame encoding an enzyme. The invention therefore provides expression cassettes or vectors useful for expressing one or more enzyme(s).

Constructs, e.g., expression cassettes, and vectors comprising the isolated nucleic acid molecule, e.g., with optimized nucleic acid sequence, as well as kits comprising the isolated nucleic acid molecule, construct or vector are also provided.

The nucleic acids described herein can also be modified to improve or alter the functional properties of the encoded enzymes. Deletions, insertions, or substitutions can be generated by a variety of methods such as, but not limited to, random mutagenesis and/or site-specific recombination-mediated methods. The mutations can range in size from one or two nucleotides to hundreds of nucleotides (or any value there between). Deletions, insertions, and/or substitutions are created at a desired location in a nucleic acid encoding the enzyme(s).

Nucleic acids encoding one or more enzyme(s) can have one or more nucleotide deletions, insertions, replacements, or substitutions. For example, the nucleic acids encoding one or more enzyme(s) can, for example, have less than 95%, or less than 94.8%, or less than 94.5%, or less than 94%, or less than 93.8%, or less than 94.50% nucleic acid sequence identity to a corresponding parental or wild-type sequence. In some cases, the nucleic acids encoding one or more enzyme(s) can have, for example, at least 50%, or at least 55%, or at least 60%, or at least 65%, or at least 70%, or at least 75%, or at least 80%, or at least 85%, or at 90% sequence identity to a corresponding parental or wild-type sequence. An example of a parental or wild type nucleic acid sequences for unmodified enzyme(s) with amino acid sequence SEQ ID NOs:1 and 3, is nucleic acid sequence SEQ ID NO:2.

Any of these nuclei acid or amino acid sequences can, for example, encode or have enzyme sequences with less than 99%, less than 98%, less than 97%, less than 96%, less than 95%, less than 94.8%, less than 94.5%, less than 94%, less than 93.8%, less than 93.5%, less than 93%, less than 92%, less than 91%, or less than 90% sequence identity to a corresponding parental or wild-type sequence.

Also provided are nucleic acid molecules (polynucleotide molecules) that can include a nucleic acid segment encoding an enzyme with a sequence that is optimized for expression in at least one selected host organism or host cell. Optimized sequences include sequences which are codon optimized, i.e., codons which are employed more frequently in one organism relative to another organism. In some cases, the balance of codon usage is such that the most frequently used codon is not used to exhaustion. Other modifications can include addition or modification of Kozak sequences and/or introns, and/or to remove undesirable sequences, for instance, potential transcription factor binding sites.

An enzyme useful for synthesis of terpenes, diterpenes, and terpenoids may be expressed on the surface of, or within, a prokaryotic or eukaryotic cell. In some cases, expressed enzyme(s) can be secreted by that cell.

Techniques of molecular biology, microbiology, and recombinant DNA technology which are within the skill of the art can be employed to make and use the enzymes, expression systems, and terpene products described herein. Such techniques available in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984): *Animal Cell Culture* (R. K. Freshney ed. 1986); *Immobilized Cells and Enzymes* (IRL press, 1986); Perbal, B., *A Practical Guide to Molecular Cloning* (1984); the series *Methods In Enzymology* (S. Colowick and N. Kaplan eds., Academic Press, Inc.); *Current Protocols In Molecular Biology* (John Wiley & Sons, Inc), *Current Protocols In Protein Science* (John Wiley & Sons, Inc), *Current Protocols In Microbiology* (John Wiley & Sons, Inc), *Current Protocols In Nucleic Acid Chemistry* (John Wiley & Sons, Inc), and *Handbook of Experimental Immunology*, Vols. I-IV (D. M. Weir and C. C. Blackwell eds., 1986, Blackwell Scientific Publications).

Prokaryotic cells can be used as host cells to express the enzymes and produce terpenes.

Modified plants and fungi that contain nucleic acids encoding enzymes within their somatic and/or germ cells are described herein. Such genetic modification can be accomplished by available procedures. For example, one of skill in the art can prepare an expression cassette or expression vector that can express one or more encoded enzymes. Plant and fungal cells can be transformed by the expression cassette or expression vector. Fungi can be generated from the fungal cells. Whole plants (and their seeds) can be generated from the plant cells that were successfully transformed with the enzyme nucleic acids. Some procedures for making such genetically modified plants and their seeds are described below.

Promoters: The nucleic acids encoding enzymes can be operably linked to a promoter, which provides for expression of mRNA from the nucleic acids encoding the enzymes. The promoter is typically a promoter functional in plants and can be a promoter functional during plant growth and development. A nucleic acid segment encoding an enzyme is operably linked to the promoter when it is located downstream from the promoter. The combination of a coding region for an enzyme operably linked to a promoter forms an expression cassette, which can optionally include other elements as well.

Promoter regions are typically found in the flanking DNA upstream from the coding sequence in both the prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning gene expression on and off in response to an exogenously added agent, or to an environmental or developmental stimulus. For example, a bacterial promoter such as the $P_{tac}$ promoter can be induced to varying levels of gene expression depending on the level of isopropyl-beta-D-thiogalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but are not limited to, examples of plant promoters such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include a CYP71D16 trichome-specific promoter and the CBTS (cembratrienol synthase) promotor, cauliflower mosaic virus promoter, the Z10 promoter from a gene encoding a 10 kD zein protein, a Z27 promoter from a gene encoding a 27 kD zein protein, the plastid rRNA-operon (rrn) promoter, inducible promoters, such as the light inducible promoter derived from the pea rbcS gene (Coruzzi et al., *EMBO J.* 3:1671 (1971)), RUBISCO-SSU light inducible promoter (SSU) from tobacco and the actin promoter from rice (McElroy et al., *The Plant Cell.* 2:163-171 (1990)). Other promoters that are useful can also be employed.

Alternatively, novel tissue specific promoter sequences may be employed. cDNA clones from a particular tissue can be isolated and those clones which are expressed specifically in that tissue can be identified, for example, using Northern blotting. Preferably, the gene isolated is not present in a high copy number but is relatively abundant in specific tissues. The promoter and control elements of corresponding genomic clones can then be localized using techniques well known to those of skill in the art.

A nucleic acid encoding an enzyme can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter or the CYP71D16 trichome-specific promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter.

The nucleic acid sequence encoding for the enzyme(s) can be subcloned downstream from the promoter using restriction enzymes and positioned to ensure that the DNA is inserted in proper orientation with respect to the promoter so that the DNA can be expressed as sense RNA. Once the nucleic acid segment encoding the enzyme is operably linked to a promoter, the expression cassette so formed can be subcloned into a plasmid or other vector (e.g., an expression vector).

In some embodiments, a cDNA clone encoding an enzyme is isolated from a mint species, for example, from leaf, trichome, or root tissue. In other embodiments, cDNA clones from other species (that encode an enzyme) are isolated from selected plant tissues, or a nucleic acid encoding a wild type, mutant or modified enzyme is prepared by available methods or as described herein. For example, the nucleic acid encoding the enzyme can be a nucleic acid with a coding region that hybridizes to SEQ ID NO:2, and that has enzyme activity. Using restriction endonucleases, the entire coding sequence for the enzyme is subcloned downstream of the promoter in a 5' to 3' sense orientation.

Targeting Sequences: Additionally, expression cassettes can be constructed and employed to target the nucleic acids encoding an enzyme to an intracellular compartment within plant cells or to direct an encoded protein to the extracellular environment. This can generally be achieved by joining a DNA sequence encoding a transit or signal peptide sequence to the coding sequence of the nucleic acid encoding the enzyme. The resultant transit, or signal, peptide can transport the protein to a particular intracellular, or extracellular, destination and can then be co-translationally or post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product within a particular location. For example, see U.S. Pat. No. 5,258,300.

For example, in some cases it may be desirable to localize the enzymes to the plastidic compartment and/or within plant cell trichomes. The best compliment of transit peptides/secretion peptide/signal peptides can be empirically ascertained. The choices can range from using the native secretion signals akin to the enzyme candidates to be transgenically expressed, to transit peptides from proteins known to be localized into plant organelles such as trichome plastids in general. For example, transit peptides can be selected from proteins that have a relative high titer in the trichomes. Examples include, but not limited to, transit peptides form a terpenoid cyclase (e.g. cembratrieneol cyclase), the LTP1 protein, the Chlorophyll a-b binding protein 40, Phyllopla-nin, Glycine-rich Protein (GRP), Cytochrome P450 (CYP71D16); all from *Nicotiana* sp. alongside RUBISCO (Ribulose bisphosphate carboxylase) small unit protein from both *Arabidopsis* and *Nicotiana* sp.

3' Sequences: When the expression cassette is to be introduced into a plant cell, the expression cassette can also optionally include 3' untranslated plant regulatory DNA sequences that act as a signal to terminate transcription and allow for the polyadenylation of the resultant mRNA. The 3' untranslated regulatory DNA sequence can include from about 300 to 1,000 nucleotide base pairs and can contain plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' untranslated regulatory sequences can be obtained as described in An (*Methods in Enzymology.* 153:292 (1987)). Many such 3' untranslated regulatory sequences are already present in plasmids available from commercial sources such as Clontech, Palo Alto, Calif. The 3' untranslated regulatory sequences can be operably linked to the 3' terminus of the nucleic acids encoding the enzyme.

Selectable and Screenable Marker Sequences: To improve identification of transformants, a selectable or screenable marker gene can be employed with the expressible nucleic acids encoding the enzyme(s). "Marker genes" are genes that impart a distinct phenotype to cells expressing the marker gene and thus allow such transformed cells to be distinguished from cells that do not have the marker. Such genes may encode either a selectable or a screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are available can be employed in the practice of the invention.

Included within the terms 'selectable or screenable marker genes' are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of an expression system that encodes a polypeptide that becomes sequestered in the cell wall, where the polypeptide includes a unique epitope may be advantageous. Such a cell wall antigen can employ an epitope sequence that would provide low background in plant tissue, a promoter-leader sequence that imparts efficient expression and targeting across the plasma membrane, and that can produce protein that is bound in the cell wall and yet is accessible to antibodies. A normally secreted cell wall protein modified to include a unique epitope would satisfy such requirements.

Example of protein markers suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich cell wall proteins (Keller et al., *EMBO J.* 8:1309-1314 (1989)) could be modified by the addition of an antigenic site to create a screenable marker.

Selectable markers for use in connection with the present invention can include, but are not limited to, a neo gene (Potrykus et al., *Mol. Gen. Genet.* 199:183-188 (1985)) which codes for kanamycin resistance and can be selected for using kanamycin, G418; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide. CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase. (Murakami et al., *Mol. Gen. Genet.* 205:42-50 (1986); Twell et al., *Plant Physiol.* 91:1270-1274 (1989)) causing rapid accumulation of ammonia and cell death. Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., Biochem. Biophys. Res. Comm. 126:1259-1268 (1985)), which may be employed in calcium-sensitive bioluminescence detection, or a green or yellow fluorescent protein gene (Niedz et al., *Plant Cell Reports.* 14:403 (1995)).

Another screenable marker contemplated for use is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also include plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUCl 19, and pUC120, pSK-derived vectors, pGEM-derived vectors, pSP-derived vectors, or pBS-derived vectors. The additional DNA sequences can include origins of replication to provide for autonomous replication of the vector, additional selectable marker genes, for example, encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al.. U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors can include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells but is usually used to transform dicot plant cells.

DNA Delivery of the DNA Molecules into Host Cells: Methods described herein can include introducing nucleic acids encoding enzymes, such as a preselected cDNA encoding the selected enzyme, into a recipient cell to create a transformed cell. In some instances, the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some recipient cells may show only initial and transient gene expression. However, certain cells from virtually any dicot or monocot species may be stably transformed, and these cells regenerated into transgenic plants, through the application of the techniques disclosed herein.

Another aspect of the invention is a plant that can produce terpenes, diterpenes sesquiterpenes, terpenoids, and combinations thereof, wherein the plant has introduced nucleic acid sequence(s) encoding one or more enzymes. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. In some embodiments, the plant or cell is a monocotyledon plant or cell. In some embodiments, the plant or cell is a dicotyledon plant or cell. For example, the plant or cell can be a tobacco plant or cell. The cell(s) may be in a suspension cell culture or may be in an intact plant part, such as an immature embryo, or in a specialized plant tissue, such as callus, such as Type I or Type II callus.

Transformation of plant cells can be conducted by any one of a number of methods available in the art. Examples are: Transformation by direct DNA transfer into plant cells by electroporation (U.S. Pat. Nos. 5,384,253 and 5,472,869, Dekeyser et al., The Plant Cell. 2:591-602 (1990)); direct DNA transfer to plant cells by PEG precipitation (Hayashimoto et al., *Plant Physiol.* 93:857-863 (1990)): direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack the functions for disease induction.

One method for dicot transformation, for example, involves infection of plant cells with *Agrobacterium tumefaciens* using the leaf-disk protocol (Horsch et al., *Science* 227:1229-1231(1985). Methods for transformation of monocotyledonous plants utilizing *Agrobacterium tumefaciens* have been described by Hiei et al. (European Patent 0 604 662, 1994) and Saito et al. (European Patent 0 672 752, 1995).

Monocot cells such as various grasses or dicot cells such as tobacco can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128.

The choice of plant tissue source for transformation may depend on the nature of the host plant and the transformation protocol. Useful tissue sources include callus, suspensions culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells.

The transformation is carried out under conditions directed to the plant tissue of choice. The plant cells or tissue are exposed to the DNA or RNA encoding enzymes for an effective period of time. This may range from a less than one second pulse of electricity for electroporation to a 2-day to 3-day co-cultivation in the presence of plasmid-bearing *Agrobacterium* cells. Buffers and media used will also vary with the plant tissue source and transformation protocol. Many transformation protocols employ a feeder layer of suspended culture cells (tobacco, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in selected plant cells. Bacteria were inactivated by ethanol dehydration prior to bombardment. A low level of transient expression of the sI-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, microprojectile bombardment does not require the isolation of protoplasts (Christou et al., *PNAS* 84:3962-3966 (1987)), the formation of partially degraded cells, and no susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing the damage inflicted on recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein, one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with the bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore, influence transformation and integration efficiencies. For example, the osmotic state, tissue hydration and the subculture stage or cell cycle of the recipient cells may be adjusted for optimum transformation. Execution of such routine adjustments will be known to those of skill in the art.

Selection: An exemplary embodiment of methods for identifying transformed cells involves exposing the bombarded cultures to a selective agent, such as a metabolic inhibitor, an antibiotic, or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/I bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations that provide 100% inhibition followed by screening of growing tissue for expression of a screenable marker gene such as luciferase would allow one to recover transformants from cell or tissue types that are not amenable to selection alone.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants to introgress the nucleic acids encoding an enzyme into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced nucleic acids, the plant is self-pollinated at least once in order to produce a homozygous backcross converted inbred containing the nucleic acids encoding the enzyme(s). Progeny of these plants are true breeding.

Alternatively, seed from transformed plants regenerated from transformed tissue cultures is grown in the field and self-pollinated to generate true breeding plants.

Seed from the fertile transgenic plants can then be evaluated for the presence and/or expression of the enzyme(s). Transgenic plant and/or seed tissue can be analyzed for enzyme expression using methods such as SDS polyacrylamide gel electrophoresis, Western blot, liquid chromatography (e.g., HPLC) or other means of detecting an enzyme product (e.g., a terpene, diterpene, sesquiterpene, terpenoid, or a combination thereof).

Once a transgenic seed or plant expressing the enzyme(s) and producing one or more terpenes, diterpenes, sesquiterpenes, and/or terpenoids in the plant is identified, the seed can be used to develop true breeding plants. The true breeding plants are used to develop a line of plants expressing terpenes, diterpenes, sesquiterpene, and/or terpenoids in various plant tissues (e.g., in leaves, bracts, and/or trichomes) while still maintaining other desirable functional agronomic traits. Adding the trait of terpene, diterpene, sesquiterpene, and/or terpenoid production can be accomplished by back-crossing with selected desirable functional agronomic trait(s) and with plants that do not exhibit such traits and studying the pattern of inheritance in segregating generations. Those plants expressing the target trait(s) in a dominant fashion are preferably selected. Back-crossing is carried out by crossing the original fertile transgenic plants with a plant from an inbred line exhibiting desirable functional agronomic characteristics while not necessarily expressing the trait of terpene, diterpene, sesquiterpenes, and/or terpenoid production in the plant. The resulting progeny can then be crossed back to the parent that expresses the terpenes, diterpenes, sesquiterpenes, and/or terpenoids. The progeny from this cross will also segregate so that some of the progeny carry the trait and some do not. This back-crossing is repeated until the goal of acquiring an inbred line with the desirable functional agronomic traits, and with production of terpenes, diterpenes, sesquiterpenes, and/or terpenoids within various tissues of the plant is achieved. The enzymes can be expressed in a dominant fashion.

Subsequent to back-crossing, the new transgenic plants can be evaluated for synthesis of terpenes, diterpenes, sesquiterpenes, and/or terpenoids in selected plant lines. This can be done, for example, by gas chromatography, mass spectroscopy, or NMR analysis of whole plant cell walls (Kim, H., and Ralph, J. Solution-state 2D NMR of ball-milled plant cell wall gels in DMSO-$d_6$/pyridine-$d_5$. (2010) *Org. Biomol. Chem.* 8(3), 576-591; Yelle, D. J., Ralph, J., and Frihart, C. R. Characterization of non-derivatized plant cell walls using high-resolution solution-state NMR spectroscopy. (2008) *Magn. Reson. Chem.* 46(6), 508-517; Kim, H., Ralph, J., and Akiyama, T. Solution-state 2D NMR of Ball-milled Plant Cell Wall Gels in DMSO-d6. (2008) *BioEnergy Research* 1(1), 56-66; Lu, F., and Ralph, J. Non-degradative dissolution and acetylation of ball-milled plant cell walls; high-resolution solution-state NMR. (2003) *Plant J.* 35(4), 535-544). The new transgenic plants can also be evaluated for a battery of functional agronomic characteristics such as lodging, yield, resistance to disease, resistance to insect pests, drought resistance, and/or herbicide resistance.

Determination of Stably Transformed Plant Tissues: To confirm the presence of the nucleic acids encoding terpene synthesizing enzymes in the regenerating plants, or seeds or progeny derived from the regenerated plant, a variety of assays may be performed. Such assays include, for example, molecular biological assays, such as Southern and Northern blotting and PCR; biochemical assays, such as detecting the presence of enzyme products, for example, by enzyme assays, by immunological assays (ELISAs and Western blots). Various plant parts can be assayed, such as trichomes, leaves, bracts, seeds or roots. In some cases, the phenotype of the whole regenerated plant can be analyzed.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced nucleic acids. PCR can also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting may be used to detect the nucleic acid encoding the enzyme(s) in question, it may not provide information as to whether the preselected DNA segment is being expressed. Expression may be evaluated by specifically identifying the protein products of the introduced nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as, native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the enzyme such as evaluation by amino acid sequencing following purification. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Hosts

Terpenes, including diterpenes and terpenoids, can be made in a variety of host organisms either in vitro or in vivo. In some cases, the enzymes described herein can be made in host cells, and those enzymes can be extracted from the host cells for use in vitro. As used herein, a "host" means a cell, tissue or organism capable of replication. The host can have an expression cassette or expression vector that can include a nucleic acid segment encoding an enzyme that is involved in the biosynthesis of terpenes.

The term "host cell", as used herein, refers to any prokaryotic or eukaryotic cell that can be transformed with an expression cassettes or vector carrying the nucleic acid segment encoding an enzyme that is involved in the biosynthesis of one or more terpenes. The host cells can, for example, be a bacterial, insect, plant, fungal, or yeast cell. Expression cassettes encoding biosynthetic enzymes can be incorporated or transferred into a host cell to facilitate manufacture of the enzymes described herein or the terpene, diterpene, or terpenoid products of those enzymes. The host cells can be present in an organism. For example, the host cells can be present in a host such as bacteria or fungi.

For example, the enzymes, terpenes, diterpenes, and terpenoids can be made in a variety of bacteria or fungal cells. The enzymes, terpenes, diterpenes, and terpenoids can be made and extracted from such cells. Enzymes can conveniently, for example, be produced in bacterial, insect, plant, or fungal (e.g., yeast) cells.

Examples of host cells, host tissues, host fungi, host seeds and plants that may be used for producing terpenes and terpenoids (e.g., by incorporation of nucleic acids and expression systems described herein). Examples include bacterial and fungal host cells. For example, the terpenes and terpenoids can be produced in bacteria as described in Shukal et al. Metabolic Engineering 55: 170-178 (2019).

The terpenes can also be produced in plants, such as those useful for production of oils such as oilseeds, camelina, canola, castor bean, corn, flax, lupins, peanut, potatoes, safflower, soybean, sunflower, cottonseed, oil firewood trees, rapeseed, rutabaga, sorghum, walnut, and various nut species. Other types host cells, host tissues, host seeds and plants that can be used include fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., poplar, pine, and eucalyptus), oil (oilseeds, camelina, canola, castor bean, lupins, potatoes, soybean, sunflower, cottonseed, oil firewood trees, rapeseed, rutabaga, sorghum), starch plants (wheat, potatoes, lupins, sunflower and cottonseed), and forage plants (alfalfa, clover and fescue). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, pine, oak, maple, walnut, rubber tree, willow, and the like. Plants useful for generating forage include legumes such as alfalfa, as well as forage grasses such as bromegrass, and bluestem. In some cases, the plant is a *Brassicaceae* or other Solanaceae species. In some embodiments, the plant is not a species of *Arabidopsis*, for example, in some embodiments, the plant is not *Arabidopsis thaliana*.

Additional examples of hosts cells and host organisms include, without limitation, tobacco cells such as *Nicotiana benthamiana, Nicotiana tabacum, Nicotiana rustica, Nicotiana excelsior*, and *Nicotiana excelsiana* cells; cells of the genus *Escherichia* such as the species *Escherichia coli*; cells of the genus *Clostridium* such as the species *Clostridium ljungdahlii, Clostridium autoethanogenum* or *Clostridium kluyveri*; cells of the genus *Corynebacterium* such as the species *Corynebacterium glutamicum*; cells of the genus *Cupriavidus* such as the species *Cupriavidus necator* or *Cupriavidus metallidurans*; cells of the genus *Pseudomonas* such as the species *Pseudomonas fluorescens. Pseudomonas putida* or *Pseudomonas oleavorans*: cells of the genus *Delftia* such as the species *Delftia acidovorans*; cells of the genus *Bacillus* such as the species *Bacillus subtilis*: cells of the genus *Lactobacillus* such as the species *Lactobacillus delbrueckii*; or cells of the genus *Lactococcus* such as the species *Lactococcus lactis*.

"Host cells" can further include, without limitation, those from yeast and other fungi, as well as, for example, insect cells. Examples of suitable eukaryotic host cells include yeasts and fungi from the genus *Aspergillus* such as *Aspergillus niger*; from the genus *Saccharomyces* such as *Saccharomyces cerevisiae*; from the genus *Candida* such as *C. tropicalis, C. albicans, C. cloacae, C. guillermondii, C. intermedia, C. maltosa, C. parapsilosis*, and *C. zeylenoides*; from the genus *Pichia* (or *Komagataella*) such as *Pichia pastoris*; from the genus *Yarrowia* such as *Yarrowia lipolytica*; from the genus *Issatchenkia* such as *Issathenkia orientalis*: from the genus *Debaryomyces* such as *Debaryomyces hansenii*; from the genus *Arxula* such as *Arxula adenoinivorans*; or from the genus *Kluyveromyces* such as *Kluyveromyces lactis* or from the genera *Erophiala, Mucor, Trichoderma, Cladosporium, Phanerochaete, Cladophialophora, Paecilomyces, Scedosporium*, and *Ophiostoma*.

In some cases, the host cells can have organelles that facilitate manufacture or storage of the terpenes, diterpenes, and terpenoids. Such organelles can include lipid droplets, smooth endoplasmic reticulum, plastids, trichomes, vacuoles, vesicles, plastids, and cellular membranes. During and after production of the terpenes, diterpenes, and terpenoids these organelles can be isolated as a semi-pure source of the of the terpenes, diterpenes, sesquiterpenes, and terpenoids.

Manufacturing

Also described herein are methods of synthesizing a terpene that include incubating a host cell that has any of the expression cassettes or expression systems described herein. For example, the terpenes and terpenoids can be produced in bacteria as described in Shukal et al. Metabolic Engineering 55: 170-178 (2019), which is incorporated by reference herein in its entirety (and provided as Appendix B).

In addition, the application includes methods of synthesizing a terpene that include cultivating a seed or plant that has any of the expression cassettes or expression systems described herein to produce a plant having terpenes in its tissues.

Such methods can also include isolation of the terpene(s) from the host cells, or the plants having terpenes in its tissues.

The terpene that is synthesized and/or isolated can be viridiflorol.

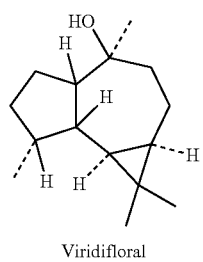

Viridifloral

Volatile organic compounds, including volatile terpenoids such as viridiflorol, mediate communication between plants and microbes (Wenke et al., 2010). Plant terpenoids have been positively involved in the development of ectomycorrhizal associations with several plant species during the pre-symbiotic phase (Fries et al., 1987: Menotta et al., 2004). Despite a couple of attempts (Crutcher et al., 2013), there is no direct evidence that fungal terpenoids could play a similar role and facilitate establishment of plant-endophytic interactions. Terpenoids produced by these fungi are most frequently implicated in defense against antagonists (Minerdi et al., 2009) or in intraspecies and interspecies recognition (Hynes et al., 2006). Colonization experiments, including experiments with knockout mutants, and antagonism assays between *S. indica* and other microorganisms such as those described herein offer a clearer image about the role of SiTPS and the produced compounds in the establishment of *S. indica*-plant association and the defense mechanisms of the endophyte.

The following Examples illustrate some of the experimental work involved in developing the invention.

Example 1: Materials and Methods

This Example describes some of the materials and methods used in the development of the invention.

Fungal and Plant Material

*Serendipita indica* (DSM11827 isolate) was grown at 28° C. in liquid complete medium (CM) (Pham et al., 2004) supplemented with 2% glucose w v$^{-1}$ and shaking at 150 rpm, or on solid CM plates (supplemented with 2% glucose w v$^{-1}$ and 1.5% w v$^{-1}$ agar).

Tomato seeds (*Solanum lycopersicum*, cv. Moneymaker) were surface sterilized with 70% ethanol for 1 min, 1% NaClO (v v$^{-1}$) for 10 min and rinsed with sterile MilliQ water. The seeds were germinated for 11 days on sterile filter paper in a growth chamber (12 h day 22° C./12 h night 18° C., 120 µE m$^{-2}$ s$^{-1}$ light intensity, 60% relative humidity). Plant inoculation with *S. indica* wild type and mutants was performed by incubating the tomato seedlings in 40 ml of fungal inoculum (300,000 chlamydospores ml$^{-1}$) overnight, on a shaker (120 rpm) at room temperature. For the control treatment, sterile water was used instead of the fungal chlamydospore suspension. After inoculation, the seedlings were sown on Murashige-Skoog (MS) Basal medium (Sigma-Aldrich, USA) supplemented with 1.5% w v$^{-1}$ agar and grown in the same growth chamber until harvesting.

Discovery of SiTPS and Phylogenetic Analysis of Putative Terpene Synthase

Figures 1, 1A, 2:
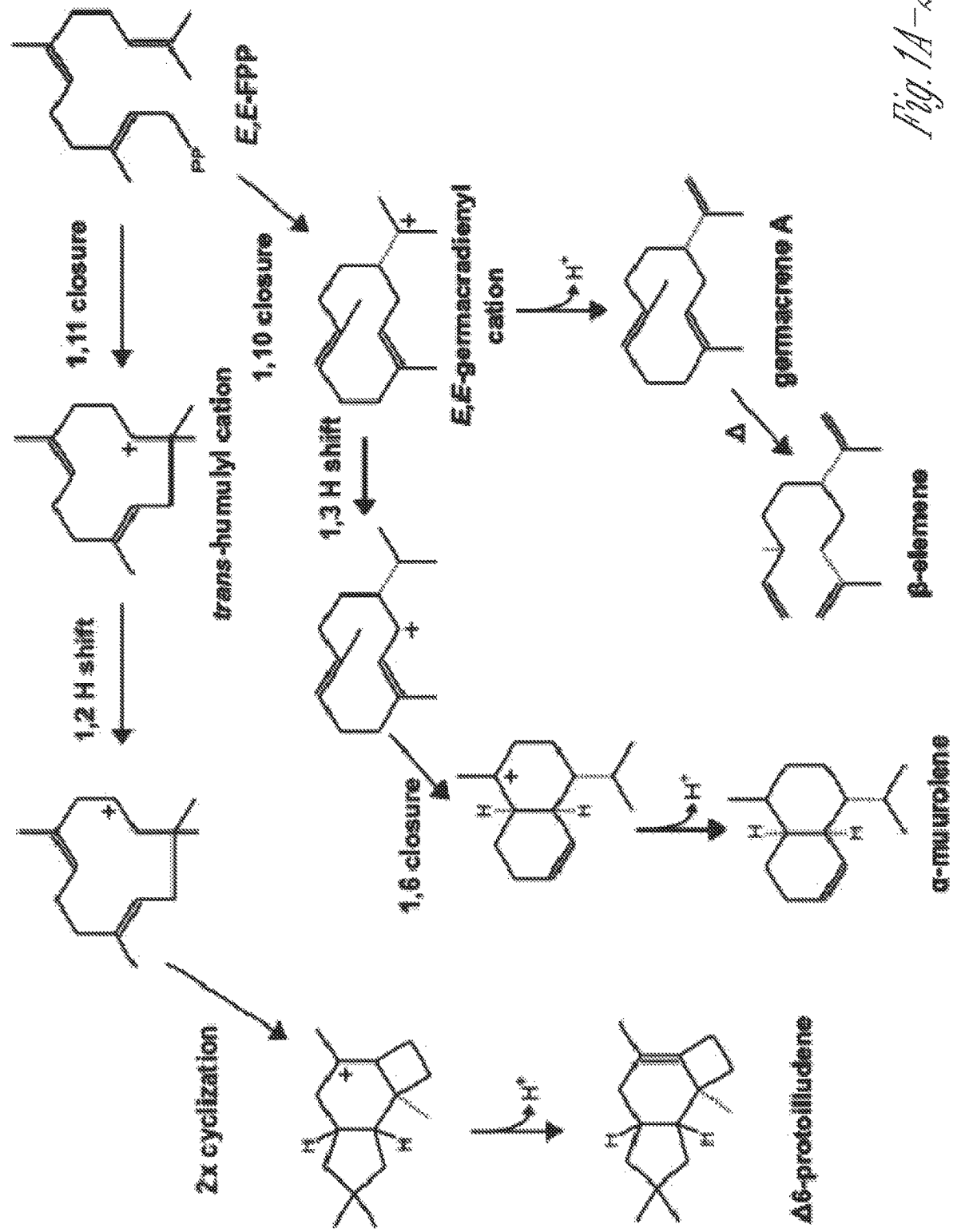
Figures 1, 1A, 2, 3:
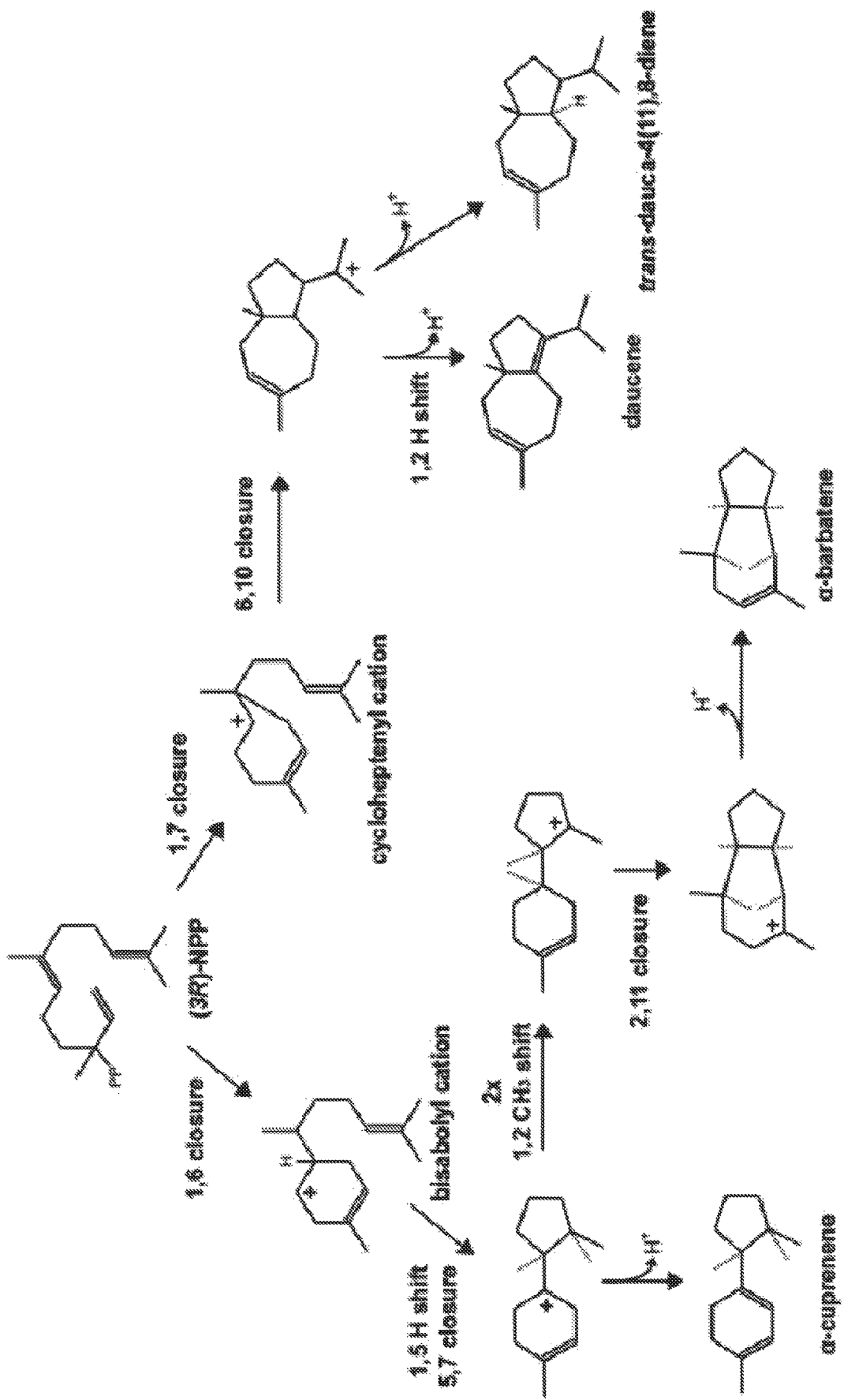

The genome of *S. indica* (available at the Joint Genome Institute-JGI website, genome.jgi.doe.gov/Pirin1/Pirin1.home.html) indicated that *S. indica* possesses one gene (JGI mRNA:PIIN_06735), which based on the annotation belongs to the Terpene_synth_C (µF03936) family (Zuccaro et al., 2011). This putative terpene synthase gene was named SiTPS and the predicted amino acid sequence (JGI Protein Id: 77541) was used in a BLASTp search in order to identify similar proteins. A selection of fungal and bacterial proteins were aligned with SiTPS sequence using the online tool GUIDANCE2 Server (see website at guidance.tau.ac.il/ver2/) (MAFFT). The alignment file was imported in MEGA7 (Kumar et al., 2016) and a maximum-likelihood phylogenetic tree (bootstrap of 100) was constructed using the default settings (FIG. 2).

SiTPS was also aligned with selected functionally characterized Basidiomycota and Ascomycota STSs, including the Cop1-6 (Agger et al., 2009; Lopez-Gallego et al., 2010a,b) and Omp1-10 (Wawrzyn et al., 2012b) using again the GUIDANCE2 Server (MAFFT). A Neighbour-joining phylogenetic tree was constructed in MEGAX (Kumar et al., 2018) (bootstrap of 100) using the default settings.

Heterologous Expression in Escherichiacoli and In Vitro Characterization of SiTPS The coding region of SiTPS (PIIN_06735) was amplified from fungal cDNA using the primers shown in Table 2.

TABLE 2

Primers

| SEQ ID NO: | Name | Sequence 5'-3' | Used for |
|---|---|---|---|
| 11 | SiTPS inf-F | AGAAGGAGATATA CCATGCCATCTGTCT CTCCTGCCAC | In-fusion ® cloning pET_SiTPS |
| 12 | SiTPS inf-R | GGTGGTGGTGCTC GAACGCAACGGGA GCCACTGGG | In-fusion ® cloning pET_SiTPS |
| 13 | TPS ovinf-F | CTCCAAAAACAGT CGATGCCATCTGTC TCTCCTGC | in-fusion ® cloning K167_SiTPS_His |
| 14 | TPS Ovinf HA-R | TAGATATCGTAG TTTGCAACGGGAGC CACTGGGGT | In-fusion ® cloning K167_SiTPS_His |
| 15 | HD1.1-F | CGATACCTACC CGCCTACAA | *S. indica* mating type locus HD 1.1 (PIN_09915) |
| 16 | HD1.1-R | CTTTTTAAGC GGTGCTGGAG | *S. indica* mating type locus HD 1.1 (PIN_09915) |
| 17 | HD2.1-R | ATGAGTACGA TTGCCCAAGG | *S. indica* mating type locus HD 2.1 (PIN_09916) |
| 18 | HD2.1-F | TCGTCTCGT AGGCGACTTTT | *S. indica* mating type locus HD 2.1 (PIN_09916) |
| 19 | HD1.2-R | AGATATCCGG AGGCGAGTTT | *S. indica* mating type locus HD 1.2 (PIN_09977) |
| 20 | HD1.2-F | CCTGAATCTG CTGTTCGTCA | *S. indica* mating type locus HD 1.2 (PIN_09977) |
| 21 | HD2.2-F | ACATCTGGCT CCCATTTACG | *S. indica* mating type locus HD 2.2 (PIN_09978) |
| 22 | HD2.2-R | GTTGAGCTTTG GCTCGTTTC | *S. indica* mating type locus HD 2.2 (PIN_09978) |
| 23 | SiITS-F | CAACACATGTG CACGTCGAT | *S. indica* ITS estimation of fungal biomass |
| 24 | SiITS-R | CCAATGTGCA TTCAGAACGA | *S. indica* ITS estimation of fungal biomass |
| 25 | SlTUB-F | AACCTCCATTC AGGAGATGTTT | *Solanum lycopersicum* β-tubulin estimation of plant biomass |
| 26 | SlTUB-R | TGCTGTAGCAT CCTGGTATT | *Solanum lycopersicum* β-tubulin estimation of plant biomass |

The coding region of SiTPS was then cloned into pET28b+ vector (Novagen) using the In-Fusion® HD Cloning Kit (Takara Bio, USA), according to manufacturer's instructions. The plasmid containing SiTPS, named pET_SiTPS, was transformed into *E. coli* C41 OverExpress™ cells (Lucigen, USA). Heterologous expression from the pET_SiTPS vector and protein purification was performed as described in Johnson et al. (2018). Briefly, 500 µl of an overnight culture (5 ml LB medium broth containing 50 µg ml$^{-1}$ kanamycin) was used to inoculate 50 ml of production medium (Terrific Broth medium [pH 7.0] containing 50 µg ml$^{-1}$ kanamycin). Cultures were grown at 37° C. in a shaking incubator (180 rpm). When the culture OD$_{600}$ reached 0.6, 100 µl of IPTG (Isopropyl β-D-1-thiogalactopyranoside, 0.2 mM) were added to induce expression. Protein expression proceeded overnight at 16° C. in a shaking incubator (180 rpm). The following day, cells were harvested by centrifugation (4500 rpm) at 4° C. for 20 min and lysed using the CelLytic B Cell Lysis Reagent (Sigma-Aldrich. USA) supplemented with 0.1 mg ml$^{-1}$ lysozyme, 10 µl ml$^{-1}$ protease inhibitor cocktail (Sigma), 0.2 mg ml$^{-1}$ benzoase, 25 mM imidazole, 500 mM NaCl and 5% v v$^{-1}$ glycerol. The cell lysate was used further for protein purification, using the His SpinTrap Kit (GE Healthcare, USA). Protein desalting was done with the PD MiniTrap G-25 desalting columns (GE Healthcare, USA) according to the manufacturer's instructions and 600 µl of desalting buffer (20 mM HEPES [pH 7.2], 1 mM MgCl$_2$, 350 mM NaCl, 5 mM DTT, and 5% v v$^{-1}$ glycerol) were used to elute the purified protein.

The in vitro terpene synthase assay was performed in a 500 µl reaction that contained 5 µg substrate (GPP, 2E,6E-FPP, or GGPP [Cayman Chemicals, USA]), 100 µg purified enzyme, 10 mM MgCl$_2$, 100 mM KCl, 5 mM DTT, and 10% v v$^{-1}$ glycerol in 50 mM HEPES (pH 7.2). The reaction was overlaid with 500 µl n-hexane. Reactions were carried out at 30° C. for 1 hour, followed by vortexing to extract the products into the organic phase. Layers were separated by centrifugation, and hexane was removed for GC-MS analysis.

In Vivo Characterization of SiTPS

For the characterization of SiTPS in vivo, two more plasmids apart from pET_SiTPS, were used. The in vivo system was established by modifying the diterpene production system previously developed by Morrone et al. (2010). The GPP synthase gene was removed from the pGG vector (Cyr et al., 2007) and replaced by a *Gallus gallus* FPP synthase gene (FPPS-Genbank XM_01529864). In detail, the *G. gallus* FPPS was synthesized (Integrated DNA Technologies, USA) and cloned into NdeI-digested and XhoI-digested pACYCDuet vector (Novagen) using the In-Fusion® HD Cloning Kit (Takara Bio, USA). The resulted plasmid was named pFF, and together with pIRS, a plasmid containing three upstream genes of the MEP pathway (Morrone et al., 2010), was introduced to *E. coli* C41 OverExpress™ cells (Lucigen, USA) to create a farnesyl diphosphate-producing strain. This strain was transformed with pET_SiTPS for the in vivo characterization of SiTPS. Transformed *E. coli* cells were grown on LB agar plates containing kanamycin (25 µg ml$^{-1}$), chloramphenicol (20 µg ml$^{-1}$), and streptomycin (25 µg ml$^{-1}$), and were further screened for the presence of all the plasmids using colony PCR. A single PCR-positive clone was grown in 50 ml Terrific Broth medium (pH 7.0), with the antibiotics mentioned above. The culture was grown at 37° C. to reach an OD$_{600}$ of 0.6, after which the temperature dropped to 16° C. for 1 hour before expression was induced with 1 mM IPTG. The culture was also supplemented with 40 mM pyruvate, 1 mM MgCl$_2$ and was grown for additional 72 hours. Produced compounds were extracted in 50 ml of n-hexane. After separation, the organic phase was concentrated under N$_2$ and analyzed by GC-MS.

Gas Chromatography-Mas Spectrometry (GC-MS) Analysis

GC-MS analysis was performed as described by Johnson et al. (2019) on an Agilent 7890A GC with an Agilent VF-5 ms column (30 m×250 µm×0.25 µm, with 10 m EZ-Guard) and an Agilent 5975C detector. The inlet was set to 250° C. splitless injection of 1 µl, helium carrier gas with column flow of 1 ml min$^{-1}$. The detector was activated after a three-minute solvent delay. The oven temperature ramp started at 80° C. hold for 1 min, increase 40° C. min$^{-1}$ to 130° C., increase 10° C. min$^{-1}$ to 250° C., increase 100° C. min$^{-1}$ to 325° C. hold 3 min. Obtained spectra were compared with NIST17 Mass Spectral Database. Analytical standards of viridiflorol (CAS 552-02-3) and ledol (CAS 577-27-5) were purchased from Sigma Aldrich (Cat No. 72999-10MG) and Santa Cruz (Cat No. sc-396548), respectively.

SiTPS Expression in Planta and in Vitro

Tomato seedlings were harvested 11 dpi (days post inoculation) and roots from seven plants were pooled together in one biological replication. Before RNA extraction, the samples were freeze-dried overnight to facilitate milling. Material from mature *S. indica* cultures, grown for two weeks on CM agar plates, was also harvested. Total RNA from root and fungal samples was extracted using the Spectrum™, Plant Total RNA Kit (Sigma-Aldrich, USA). cDNA was synthesized with the Revert First Strand cDNA Synthesis kit and an oligo-dT primer (Thermo Fisher Scientific, USA).

For the RT-qPCR, 600 ng of cDNA was used as a template in a 10 µl reaction, using 5 µl of the Brilliant III Ultra-Fast SYBR® Green (Agilent Technologies, USA) and SiTPS-specific primers (Table 2). Each RT-qPCR reaction was performed with three technical replications for the four biological replications. RT-qPCR was performed using the AriaMx Real-Time PCR System-G8830A (Agilent Technologies, USA) with a program of 95° C. for 5 min, followed by 40 cycles of 95° C. for 30 sec, 60° C. for 1 min, and 72° C. for 1 min. A final dissociation step was performed to assess the quality of amplified products and the specificity of the primers. Expression of SiTPS was normalized using *S. indica* glyceraldehyde-3-phosphate dehydrogenase gene (GAPDH. GenBank: FJ810523.1) expression levels and calculated with the 2$^{-\Delta Ct}$ method (Livak & Schmittgen, 2001; Schmittgen & Livak, 2008).

Figure 6:
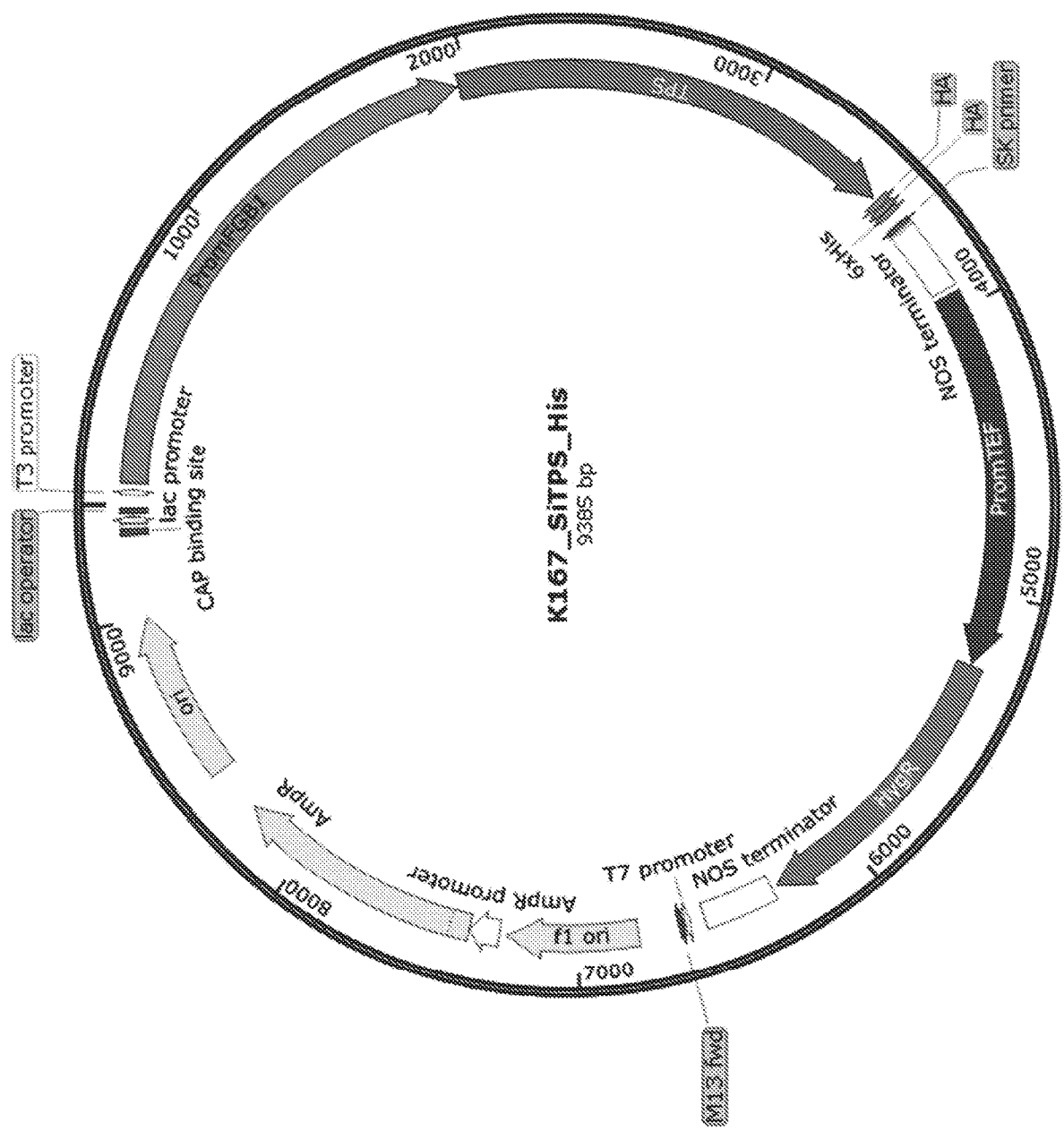
FIG. 6 is a schematic diagram illustrating the structure of the plasmid K167_PromFCGBI_SiTPS_His used for creating the SiTPS-overexpressing mutants. The vector backbone is comprised of a hygromycin marker cassette and an ampicillin-resistance gene. The SiTPS sequence is HA- and His-tagged. Gene expression is under the control of the promoter FCGB1 of *S. indica*.

Construction of Overexpression Plasmids and *P. indica* PEG-Mediated Transformation For creating a SiTPS-overexpressing mutant, SiTPS coding sequence was cloned into NheI and PmeI digested K167 vector (Wawra and Widmer, unpublished) using the In-Fusion® HD Cloning Kit (Takara Bio, USA), resulting to the plasmid K167_SiTPSov (FIG. 6). The empty vector named K167_ev was also used for *S. indica* transformation as a control-treatment.

*S. indica* protoplasts were isolated and transformed with K167_SiTPSov and K167_ev through polyethylene glycol (PEG)-mediated transformation according to Hilbert et al., 2012. Young mycelium from a 7-day-old *S. indica* culture was harvested, crushed and left to regenerate for three further days. The regenerated mycelium was treated with 20 ml solution (1.33 M sorbitol, 50 mM CaCl2 and 20 mM MES) containing 0.02 g ml$^{-1}$ lysing enzyme from *Trichoderma harzianum* (Sigma-Aldrich, USA) at 32° C. After 2 h, protoplasts were harvested and transformed with 7-10 µg of linearized and purified plasmid in the presence of 40% PEG 3350 and heparin (15 mg ml$^{-1}$). Protoplast regeneration was done using plates with two layers of malt yeast peptone (MYP) agar supplemented with 0.3 M sucrose (0.7% w v$^{-1}$ malt extract, 0.1% w v$^{-1}$ peptone, 0.05% w v$^{-1}$ yeast extract). The bottom medium contained 1.2% agar and hygromycin B (80 µg ml$^{-1}$). The top medium (0.6% agar and no antibiotics) was mixed with the transformation mixture and then quickly poured on to the solidified bottom medium. The plates were incubated at 28° C. After 10-14 days, regenerated colonies were transferred to CM plates supplemented with 80 µg/ml hygromycin B and checked for carrying either K167_SiTPS or K167_EV. *S. indica* mutants used for further studies were selected based on their growth and their mating type.

Quantification of Root Colonization by *S. indica* and Mutants with qPCR

Genomic DNA was extracted from root samples of inoculated tomato plants 2- and 11-days post inoculation (dpi) using the DNeasy® Plant Mini Kit (Qiagen, Germany). Roots from 8 plants were pooled in one biological replication and 3 biological replications were included per timepoint, per treatment. The qPCR was performed in the AriaMx Real-Time PCR System-G8830A (Agilent Technologies, USA) using a cycling program of 95° C. for 5 min, 30 cycles of 95° C. for 30 sec, 62° C. for 1 min, and 72° C. for 1 min. A final dissociation step was performed to assess the quality of amplified products and the specificity of the primers. In a 10 µl reaction, 5 µl of the Brilliant III Ultra-Fast SYBR® Green (Agilent Technologies, USA), 1 µl of total DNA and 0.4 µM of plant- or fungus-specific primers were used (Table 2).

Fungal colonization was determined using the ratio of fungal to plant DNA amount. For the quantification of fungal DNA, a standard curve, made using serial dilutions of DNA from an *S. indica* pure culture and specific primers (SiITS, GenBank: NR_119580.1), was used. Plant DNA was quantified similarly, using a standard curve of plant DNA dilutions and specific primers (SITUB, GenBank: DQ205342.1).

Example 2: Phylogenetic Analysis on SiTPS

The phylogenetic analysis using proteins with the highest sequence similarity to SiTPS (FIG. 2) showed that its closest relative is a terpenoid synthase, found in the orchid mycorrhizal fungus *Serendipita vermifera* (previously known as *Sebacina vermifera*) belonging to the same genus. However, the activity of *S. vermifera* terpenoid synthase remains unknown giving also no information about SiTPS function. Closely related to these two *Sebacinales* TPSs appeared to be a protein from the lichen *Cladonia uncialis*, annotated as a putative pentalenene synthase (Bertrand et aL, 2018). No experimental evidence on the function of this enzyme is available either.

The phylogenetic tree constructed from a selection of characterized fungal STSs including Cop1-6 (Agger et aL, 2009; Lopez-Gallego et al., 2010a), Omp1-10, Fompi 1 (Wawrzyn et al., 2012b), Stehi11159379, 128017, 25180, 64702, 73029 (Quin et al., 2015; Flynn & Schmidt-Dannert, 2018) and more, revealed that these enzymes fall in one of the four distinct STS clades. SiTPS is a member of Clade I, which includes STSs that catalyze formation of sesquiterpenoids through an initial C1-C10 closure of 2E,6E-FPP.

The phylogenetic analysis on SiTPS-related amino acid sequences (FIG. 2) showed that the closer relative to SiTPS is the terpenoid synthase from *S. vermifera*, also a member of the *Sebacinales* order (Ray et aL, 2018). However, since the gene from *S. vermifera* has not been functionally characterized, it is not clear whether clustering of the two terpenoid synthases occurred due to taxonomical reasons or similar functions.

In addition, this phylogenetic analysis indicates that a clear separation exists between fungal and bacterial sequences. The fungal cluster included proteins only from species of the Basidiomycota phylum, namely plant-symbionts e.g. *S. vermifera* and *Tulasnella calospora* (orchid symbionts) or decomposers of plant material [wood-rotting (*Grifola frondosa*, *Gloeophyllum trabeum*) and saprophytic fungi (*Rhizoctonia solani*). However, one of the terpenoid synthases (AUW30846.1) found in the fungal cluster, and actually closely-related to the *Sebacinales* cluster, belongs to the lichen *Cladonia uncialis*.

Lichens comprise symbiotic events between an autotroph organism (algae or cyanobacteria) and a fungal partner. Lichenized fungi are phylogenetically widespread in the two phyla, Ascomycota and Basidiomycota (Yuan, 2005). However, the genus *Cladonia* includes only Ascomycota lichenized fungi (Wang et al., 2011), meaning that AUW30846.1 is the only representative of the Ascomycota phylum in the fungal cluster (FIG. 2). This indicates that similarity between the lichen TPS and the *Sebacinales* TPSs is not due to taxonomical proximity between the organisms, but functional convergence.

Recently, the fungal symbiont of *C. uncialis* was isolated and its genome was sequenced, revealing 48 secondary metabolite biosynthetic clusters and a vast potential for production of natural products. However, *C. uncialis* is known to produce only usnic acid, indicating that most of these gene clusters remain inactive under lab-culturing conditions. Among these clusters, nine terpene synthases were identified (Cu-terp-1 to 9) and the gene product of Cu-terp-1 was the only one closely related to SiTPS (AUW30846.1). Based on sequence similarity to GenBank characterized genes, Cu-terp-I was proposed to be a pentalenene synthase (Bertrand et al., 2018). However, its function has not been validated experimentally.

A sequence for the *Cladonia uncialis* pentalenene synthase with accession number AUW30846.1 is shown below as SEQ ID NO:5.

```
  1   MCAEWITVLF VWDDLLLDVPI DSDLVSDEQG TREINRVMSC
 41   ILTQPENFEP MVTQPVTGAL HSFWTQFCAT SSPNMQKRFV
 81   EAVLKYAEGA AKQVASRETR ALPSIKDFIV NRQSASGVET
121   LLALVEYCLQ IQVPDCAYYH PTLQQLRNSI NEIVSWSNDI
161   YSFNKEQACG DHANLVVVVA IEKGIPVQSA ITYVSVMVQE
201   AVKRYHENLK KIPKFDPRID ALVLKYVGGI ECVCTGLVSW
241   HFKIDRYFGE NSSEVSNTLM VDLLPQEKNA LVSAHELQYD
281   QLPISTPQPK GSAMT
```

Example 3: SiTPS Encodes a Viridiflorol Synthase

SiTPS biochemical activity was elucidated using in vitm assays and an *E. coli*-based in vivo terpene production system. In the in vitro assays the purified SiTPS, heterologously produced in *E. coli* cultures, was fed with three terpene substrates (GPP, 2E,6E-FPP, GGPP). Hexane was used to overlay the reactions and extract the produced compounds.

Figure 3A:
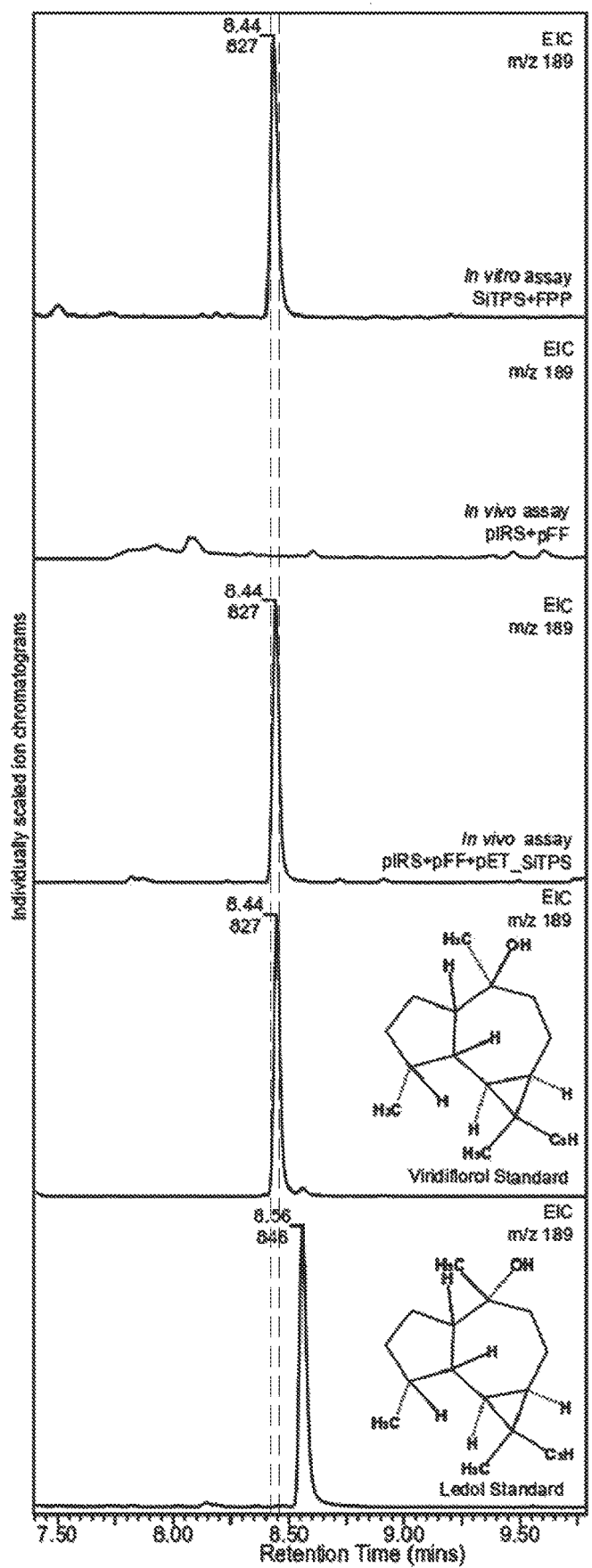
FIG. 3A-B illustrates in vivo and in vitro characterization of assay for SiTPS enzyme activity, as detected by gas chromatography-mass spectroscopy (GC-MS) analysis of hexane extracts of the assay reactions. The in vitro assay included incubation of the purified SiTPS with the substrate FPP, while the in vivo assay included use of *E. coli* strains transformed with the plasmids pIRS, pFF and pET_SiTPS. An *E. coli* strain carrying only the pIRS and pFF plasmids was used as control. Analytical standards of viridiflorol and ledol are also shown.

An *E. coli*-based in vivo system was used to validate results from the in vitro assays. The *E. coli* cells were transformed with the plasmids pFF and pIRS, resulting to an FPP-producing system. Finally, these FPP-producing strains were transformed with pET_SiTPS. After protein expression was completed, the *E. coli* cultures were extracted with hexane. GC-MS analysis on the hexane extract from the *E. coli* expression system with all three plasmids (pIRS, pFF and pET_SiTPS) showed a number of peaks that were absent in the extract derived from the FPP-producing control (FIG. 3A). One peak, at 8.44 mins, was the most intense and considered to be the main product (FIG. 3A). The retention time and the mass spectrum of this unique peak matched one of the products of the in vitro assay with SiTPS and 2E,6E-FPP. A NIST17 database search showed that the closest matches were the sesquiterpenes viridiflorol and ledol, but the retention time and the mass spectrum of SiTPS product were identical to that of the viridiflorol standard.

Figure 3B:
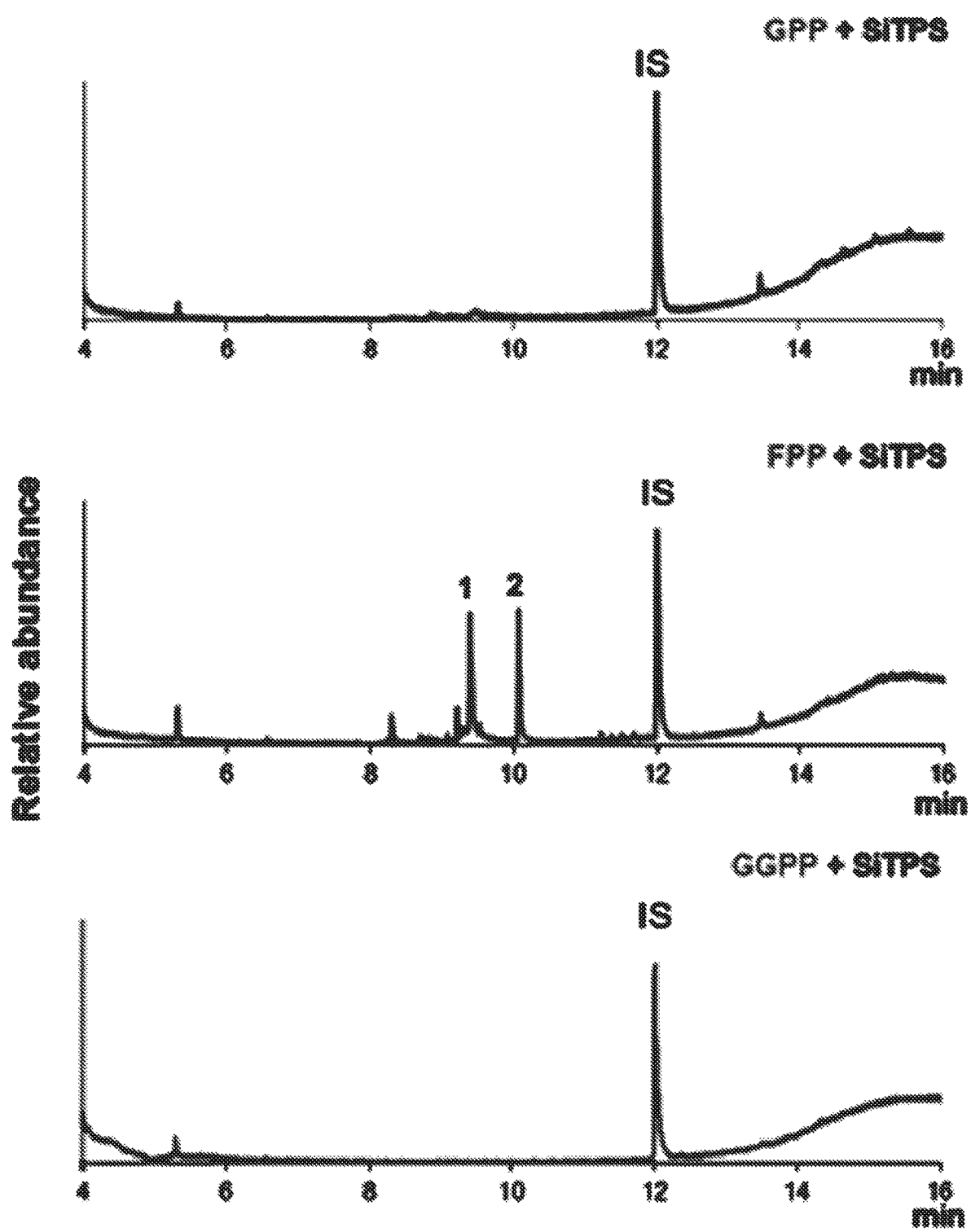
Figure 4:
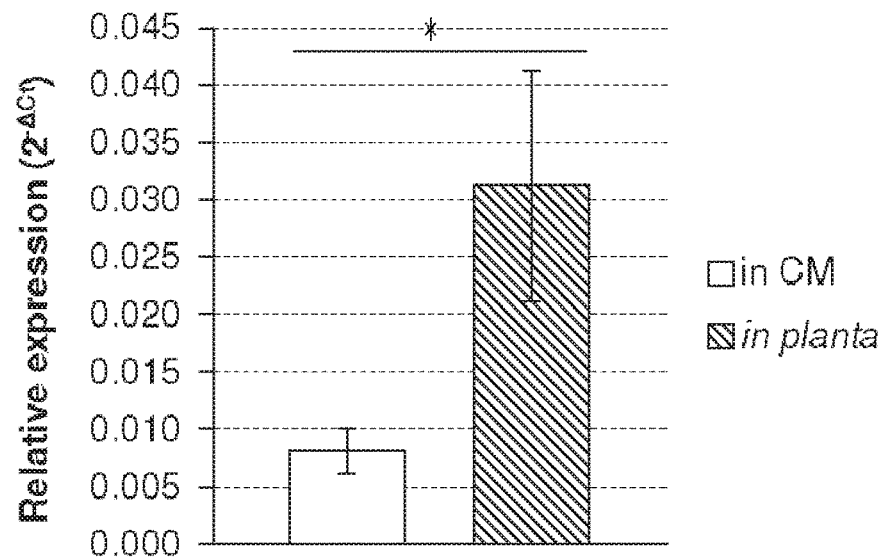

FIG. 3A shows chromatographic separation of the SiTPS products. As illustrated in FIG. 3B, SiTPS showed activity only when it was incubated with FPP, validating its NCBI annotation as a "conventional" sesquiterpene synthase.

The in vitro and in vivo characterization assays showed that SiTPS is using FPP to produce a mix of sesquiterpenoids with the main product identified as viridiflorol (FIG. 3A). Viridiflorol is a sesquiterpenoid with a 7/5/3 tricyclic scaffold and belongs to the group of aromadendranes, terpenoids with a characteristic skeleton of a dimethyl cyclopropane ring fused to a hydroazulene ring system (Gijsen et al., 1992).

Figures 1, 1A, 2, 3, 4:
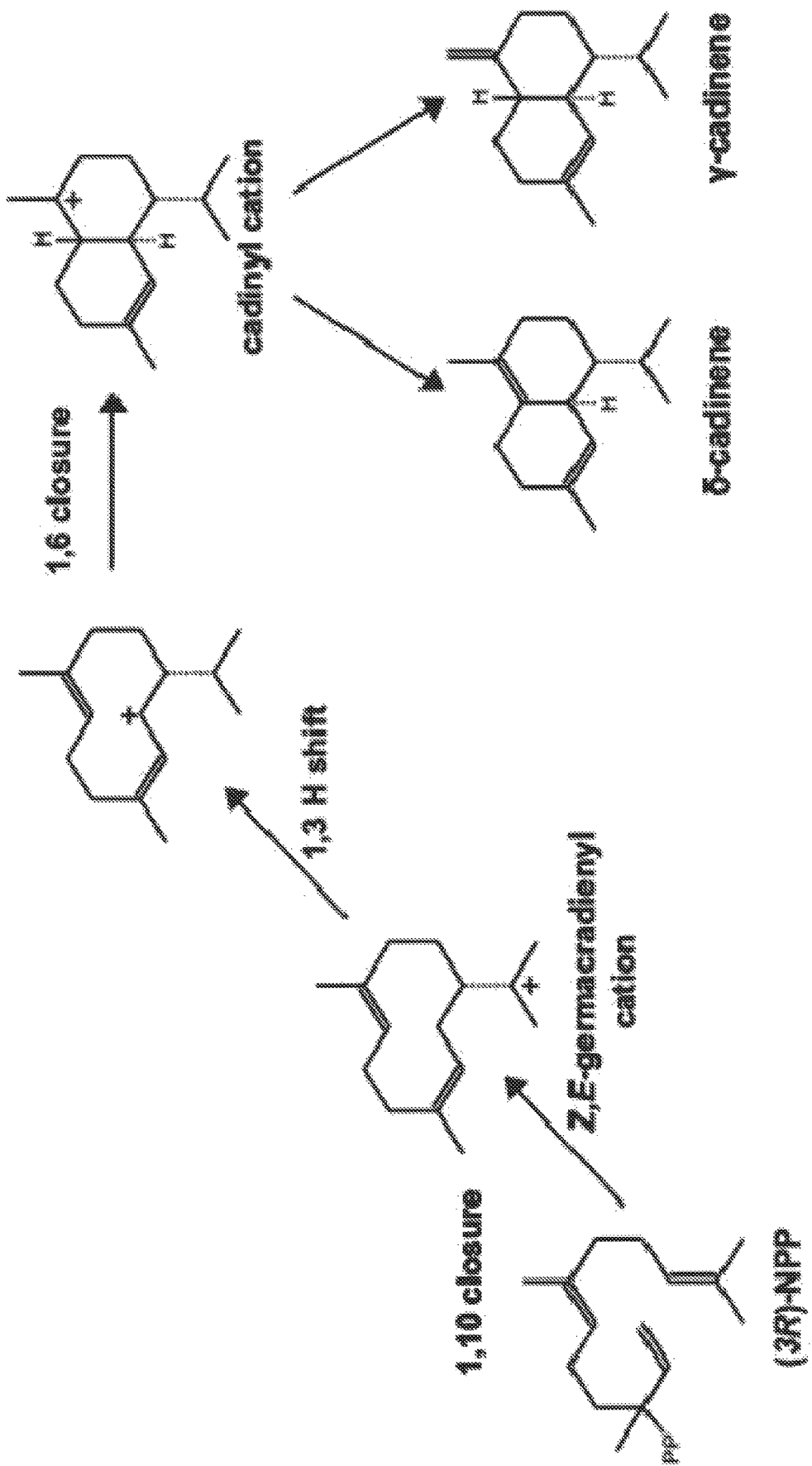
Figures 1, 1B:
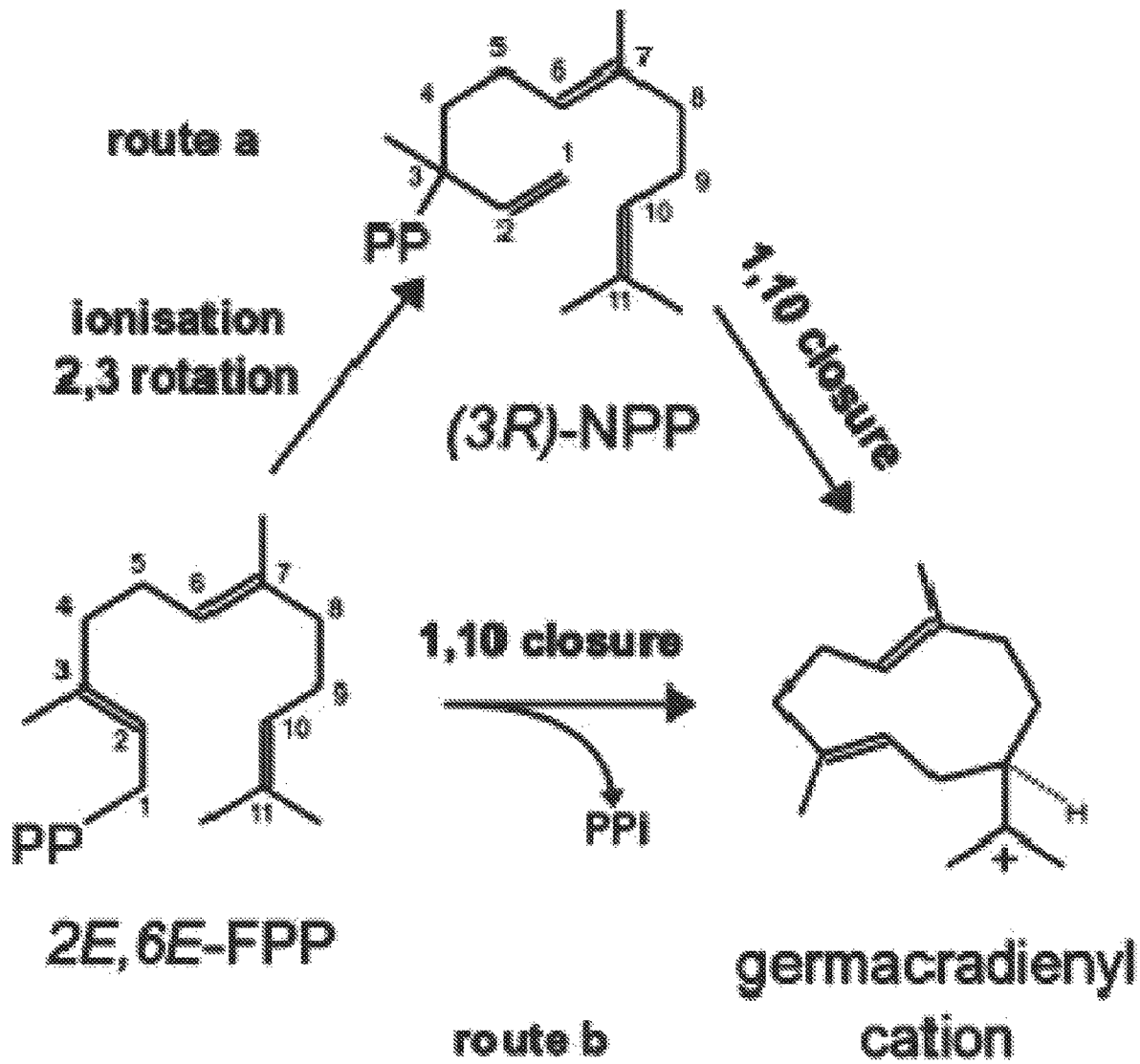
Figures 1, 1B, 2:
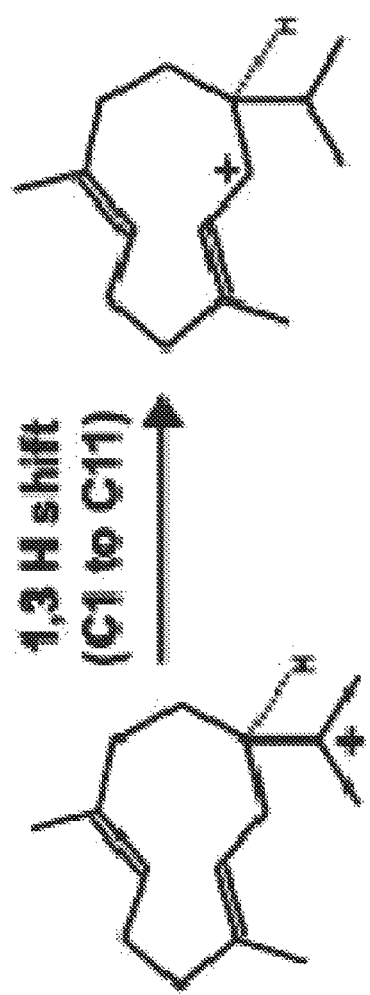
Figures 1, 1B, 2, 3:
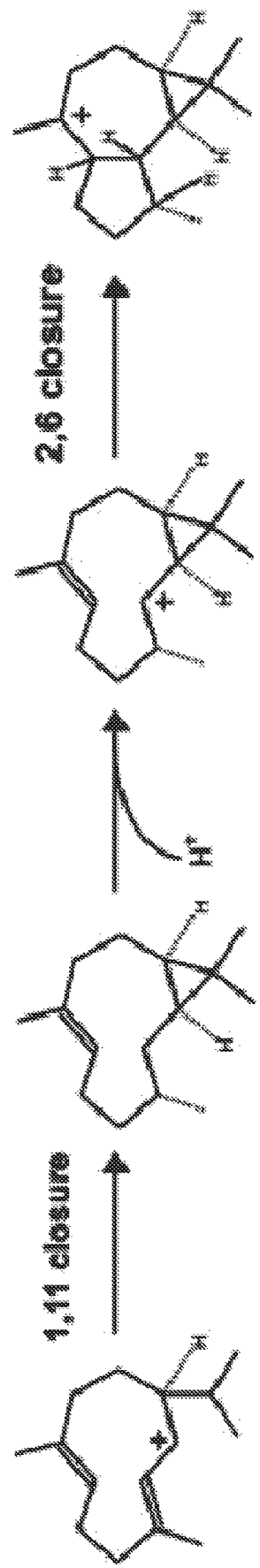
Figures 1, 1B, 2, 3, 4:
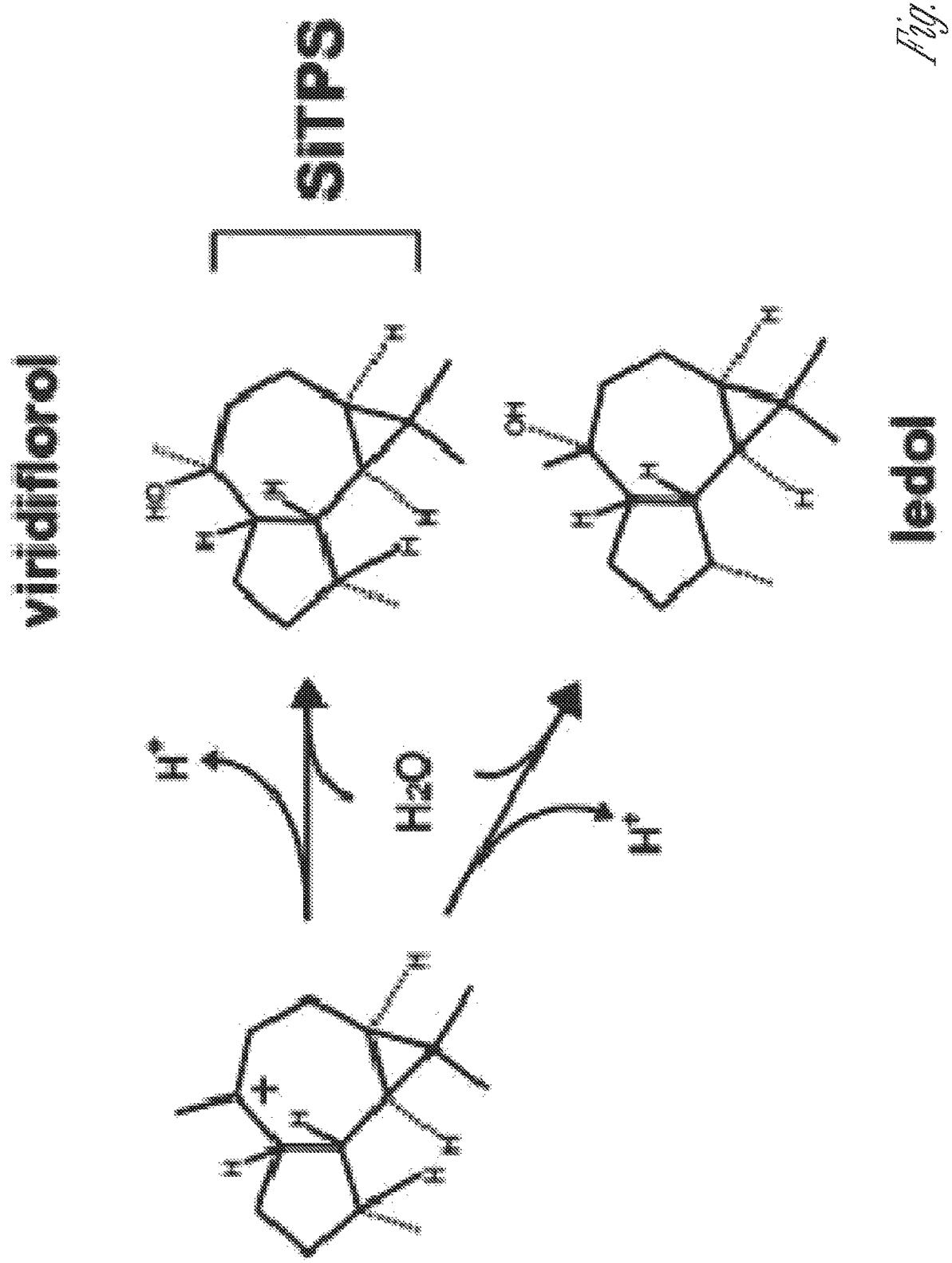
Figure 2:
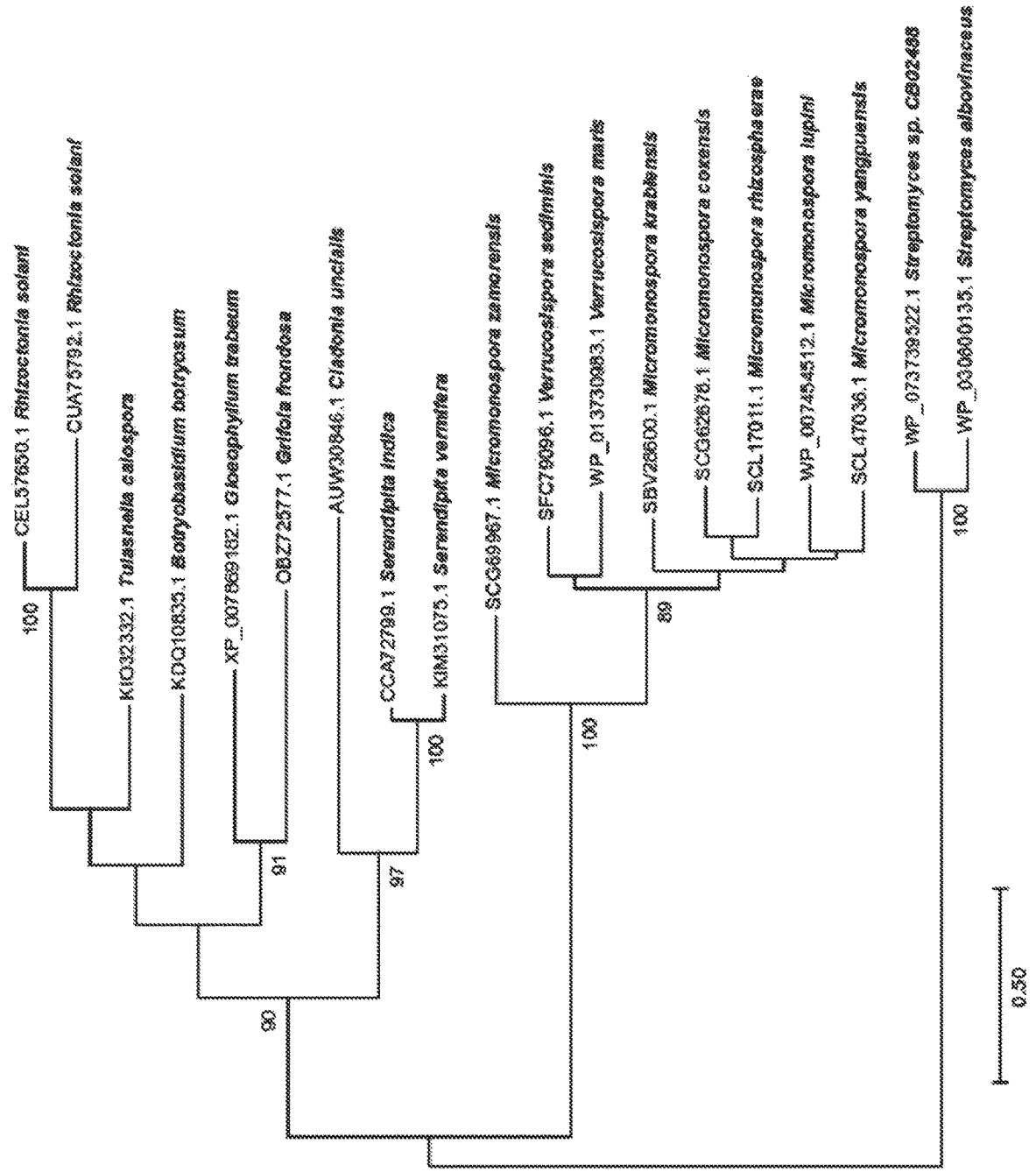

One mechanism for the formation of viridiflorol starts with the cyclization of FPP by a ring closure of C1 and C10 (FIG. 1B: see also, Hong & Tantillo (2011)). However, it is possible that FPP cyclisation occurs either with the 1,10 closure of 2E,6E-FPP (route b) or its isomer, (3R)-NPP (route a). More likely, SiTPS acts through route b, since phylogenetic analysis showed that it belongs to Clade I of STSs, which includes enzymes that form sesquiterpenes by preferably catalyzing 1,10 cyclisation of 2E,6E-FPPcarbocation (FIG. 1B).

Viridiflorol has been detected in extracts of many plant species of the Myrtaceae (Padovan et al., 2010; Dreher et al., 2019) and the Lamiaceae families (Medjahed et al., 2016; Ramirez et al., 2018). However, only two proteins from the plant *Melaleuca quinquenervia* have been identified as viridiflorol synthases (Padovan et al., 2010). Viridiflorol has also been encountered as a minor product in fungal extracts (Meshram et al., 2014; Wu et al., 2016), but there was no viridiflorol synthase gene of a fungal origin reported until now. SiTPS is the first fungal viridiflorol synthase identified and characterized experimentally.

Example 4: SiTPS is Induced Upon Root-Colonization

Expression of SiTPS was studied under two different growing conditions. Relative expression of SiTPS was quantified in fungal material from 14-day-old *S. indica* colonies, grown on synthetic medium (here CM agar), and the characteristics thereof were compared to SiTPS expressing fungi-colonized tomato roots at 11 days post inoculation (FIG. 4). SiTPS gene expression was up-regulated 3-fold when *S. indica* was growing in planta instead of on CM agar plates. Hence, a moderate induction of SiTPS expression was observed when the *S. indica* fungus is associated with plant tissues.

Example 5: SiTPS Implication in Colonization of Tomato Roots

Even though SiTPS was shown to express a functional viridiflorol synthase in *E. coli* expression systems, no terpenoid was detected in *S. indica* cultures (data not shown). However. SiTPS was upregulated upon root colonization (FIG. 4). These data indicated that SiTPS products may play a role in *S. indica* and plant root interactions.

To investigate if SiTPS can play a role in the ability of the fungus to colonize plant roots, *S. indica* mutants that over-expressed SiTPS were constructed. *S. indica* protoplasts were transformed with a K167 plasmid carrying a SiTPS coding sequence under the control of a strong promoter (FGB1 promoter-Fungal Glucan-Binding 1, PIIN_03211) (FIG. 6).

Figure 7:
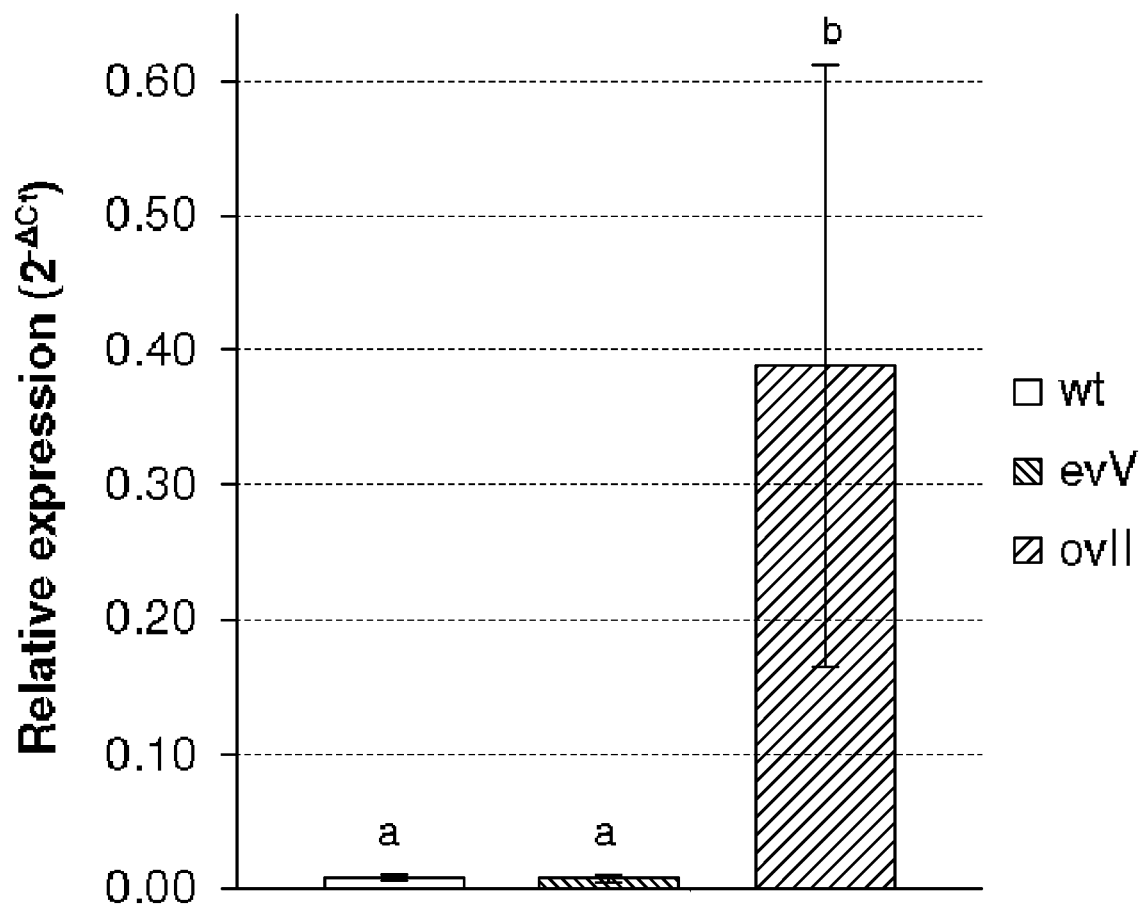
FIG. 7 graphically illustrates the relative expression of SiTPS in the following *S. indica* strains wild type (wt, left bar); empty vector strain-transformant V (evV, middle bar); and SiTPS-overexpressing strain-transformant 11 (ovII, right bar) after growth for 14 days on CM agar plates. Relative expression was normalized using SiGAPDH (GenBank: FJ810523.1) expression levels and calculated with the $2^{-\Delta Ct}$ method (Livak & Schmittgen, 2001; Schmittgen & Livak, 2008). Error bars represent the standard deviation (n=4). Different letters indicate statistical differences (t-test in Rstudio, P-value≤0.05).

After a screening of the regenerative clones, one SiTPS-overexpressing transformant (ovII) was selected and used in time-course colonization experiments to evaluate its ability to colonize plant roots. An *S. indica*-transformant carrying the empty K167 vector (control treatment-evV) and the wild type *S. indica* were also used in the same colonization studies (FIG. 7).

Figure 5:
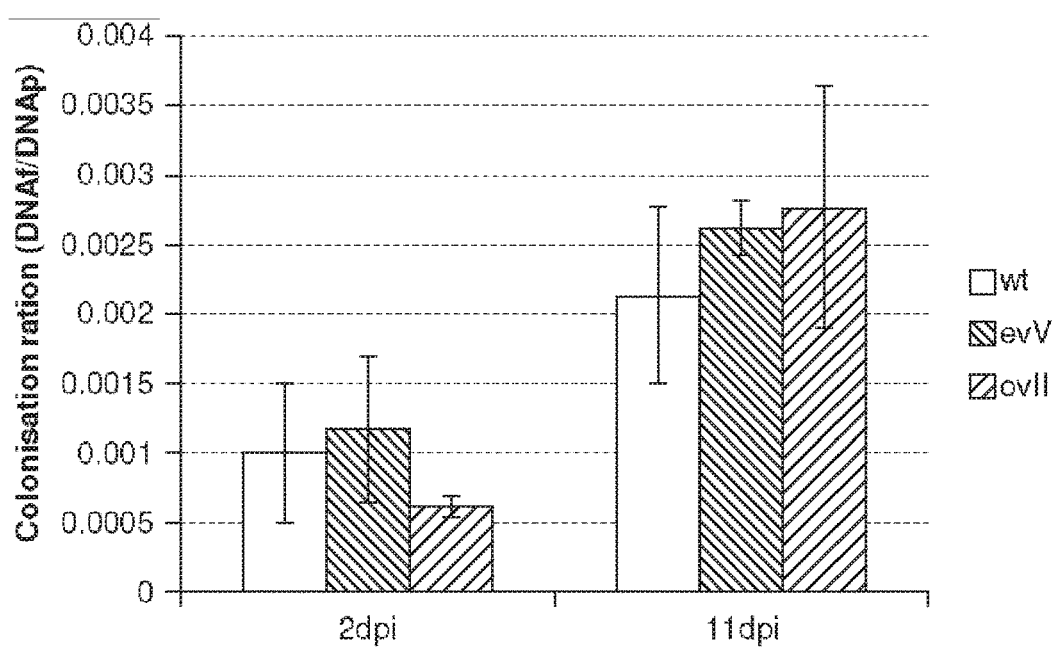
FIG. 5 graphically illustrates the colonisation ability of *S. indica* wild type (wt, left bars), *S. indica* expressing an empty vector (evV, middle bars), and *S. indica* over-expressing the SiTPS enzyme (ovII, right bars) at 2 days post inoculation (dpi). To measure the ability of to colonise plant roots the colonisation ratio, the ratio of fungal to plant DNA (DNAf/DNAp), was used. No statistical difference was observed between the different treatments (one-way ANOVA).

The ratio of fungal DNA to plant DNA was used as a measurement of the colonization ability of each *S. indica* transformant. Colonization ratios were estimated in colonized roots 2- and 11-days post-inoculation. No difference was observed in the colonization ability between the SiTPS-over-expressing transformants, the empty vector-carrying transformants, and the wild type at the selected time-points. No difference was observed in colonization ability between *S. indica* transformants and the wild type either (FIG. 5).

REFERENCES

Agger S, Lopez-Gallego F, Schmidt-Dannert C. 2009. Diversity of sesquiterpene synthases in the basidiomycete *Coprinus cinereus*. *Molecular Microbiology* 72: 1181-1195.

Bajaj R, Huang Y, Gebrechristos S, Mikolajczyk B, Brown H, Prasad R, Varma A, Bushley K E. 2018. Transcriptional responses of soybean roots to colonization with the root endophytic fungus *Piriformospora indica* reveals altered phenylpropanoid and secondary metabolism. *Scientific Reports* 8: 10227.

Bertrand R L, Abdel-Hameed M, Sorensen J L. 2018. Lichen Biosynthetic Gene Clusters. Part 1. Genome Sequencing Reveals a Rich Biosynthetic Potential. *Journal of Natural Products* 81: 723-731.

Blackwell M. 2011. The Fungi: 1, 2, 3 . . . 5.1 million species? *American Journal of Botany* 98: 426-438.

Brock N L. Huss K, Tudzynski B, Dickschat J S. 2013. Genetic Dissection of Sesquiterpene Biosynthesis by *Fusarium fujikuroi*. *ChemBioChem* 14: 311-315.

Caruthers J M, Kang 1, Rynkiewicz M J, Cane D E, Christianson D W. 2000. Crystal Structure Determination of Aristolochene Synthase from the Blue Cheese Mold, Penicillium roqueforti*. *Journal of Biological Chemistry* 275: 25533-25539.

Christianson D W. 2006. Structural Biology and Chemistry of the Terpenoid Cyclases. *Chemical Reviews* 106: 3412-3442.

Crutcher F K, Parich A, Schuhmacher R, Mukherjee P K, Zeilinger S, Kenerley C M. 2013. A putative terpene cyclase, vir4, is responsible for the biosynthesis of volatile terpene compounds in the biocontrol fungus *Trichoderma virens*. *Fungal Genetics and Biology* 56: 67-77.

Cyr A. Wilderman P R, Determan M, Peters R J. 2007. A Modular Approach for Facile Biosynthesis of Labdane-Related Diterpenes. *Journal of the American Chemical Society* 129: 6684-6685.

Dreher D, Baldermann S, Schreiner M, Hause B. 2019. An arbuscular mycorrhizal fungus and a root pathogen induce different volatiles emitted by *Medicago truncatula* roots. *Journal of Advanced Research*: 0-5.

Engels B, Heinig U, Grothe T, Stadler M, Jennewein S. 2011. Cloning and Characterization of an *Armillaria gallica* cDNA Encoding Protoilludene Synthase, Which Catalyzes the First Committed Step in the Synthesis of Antimicrobial Melleolides. *Journal of Biological Chemistry* 286: 6871-6878.

Flynn C M, Broz K, Jonkers W, Schmidt-Dannert C, Kistler H C. 2019. Expression of the *Fusarium graminearum* terpenome and involvement of the endoplasmic reticulum-derived toxisome. *Fungal Genetics and Biology* 124: 78-87.

Flynn C M, Schmidt-Dannert C. 2018. Sesquiterpene Synthase-3-Hydroxy-3-Methylglutaryl Coenzyme A Synthase Fusion Protein Responsible for Hirsutene Biosynthesis in *Stereum hirsutum* (C Vieille, Ed.). *Applied and Environmental Microbiology* 84: 1-18.

Fries N, Serck-Hanssen K, Dimberg L H, Theander O. 1987. Abietic acid, and activator of basidiospore germination in ectomycorrhizal species of the genus Suillus (Boletaceae). *Experimental Mycology* 11: 360-363.

Furtado F, Borges B, Teixeira T, Garces H, Almeida Junior L, Alves F, Silva C, Fernandes Junior A. 2018. Chemical Composition and Bioactivity of Essential Oil from Blepharocalyx salicifolius. *International Journal of Molecular Sciences* 19: 33.

Gershenzon J. Dudareva N. 2007. The function of terpene natural products in the natural world. *Nature Chemical Biology* 3: 408-414.

Gijsen HJM, Wijnberg JBPA, Stork G A, de Groot A, de Waard M A, van Nistelrooy JGM. 1992. The synthesis of mono- and dihydroxy aromadendrane sesquiterpenes, starting from natural (+)-aromadendrene-III. *Tetrahedron* 48: 2465-2476.

Hilbert M, Voll L M, Ding Y, Hofmann J, Sharma M, Zuccaro A. 2012. Indole derivative production by the root endophyte Piriformospora indica is not required for growth promotion but for biotrophic colonization of barley roots. *New Phytologist* 196: 520-534.

Hohn T M, Beremand P D. 1989. Isolation and nucleotide sequence of a sesquiterpene cyclase gene from the trichothecene-producing fungus *Fusarium sporotrichioides*. *Gene* 79: 131-138.

Hong Y J, Tantillo D J. 2011. How Many Secondary Carbocations Are Involved in the Biosynthesis of Avermitilol? *Organic Letters* 13: 1294-1297.

Hynes J, Müller C T, Jones T H, Boddy L. 2006. Changes in Volatile Production During the Course of Fungal Mycelial Interactions Between Hypholoma fasciculare and Resinicium bicolor. *Journal of Chemical Ecology* 33: 43-57.

Jacobs S, Zechmann B, Molitor A. Trujillo M, Petutschnig E, Lipka V, Kogel K-H, Schafer P. 2011. Broad-Spectrum Suppression of Innate Immunity Is Required for Colonization of Arabidopsis Roots by the Fungus Piriformospora indica. *PLANT PHYSIOLOGY* 156: 726-740.

Johnson S R, Bhat W W, Bibik J, Turmo A, Hamberger B, Hamberger B. 2019a. A database-driven approach identifies additional diterpene synthase activities in the mint family (Lamiaceae). *Journal of Biological Chemistry* 294: 1349-1362.

Johnson S R, Bhat W W, Sadre R, Miller G P, Garcia A S, Hamberger B. 2019b.

Promiscuous terpene synthases from Prunella vulgaris highlight the importance of substrate and compartment switching in terpene synthase evolution. *New Phytologist*: nph.15778.

Kumar S, Stecher G, Li M, Knyaz C, Tamura K. 2018. MEGA X: Molecular Evolutionary Genetics Analysis across Computing Platforms (F U Battistuzzi, Ed.). *Molecular Biology and Evolution* 35: 1547-1549.

Kumar S, Stecher G, Tamura K. 2016. MEGA7: Molecular Evolutionary Genetics Analysis Version 7.0 for Bigger Datasets. *Molecular Biology and Evolution* 33: 1870-1874.

Livak K J. Schmittgen T D. 2001. Analysis of Relative Gene Expression Data Using Real-Time Quantitative PCR and the 2-ΔΔCT Method. *Methods* 25: 402-408.

Lopez-Gallego F, Agger S A, Abate-Pella D, Distefano M D, Schmidt-Dannert C. 2010a. Sesquiterpene Synthases Cop4 and Cop6 from Coprinus cinereus: Catalytic Promiscuity and Cyclization of Farnesyl Pyrophosphate Geometric Isomers. *ChemBioChem* 11: 1093-1106.

Lopez-Gallego F, Wawrzyn G, Schmidt-Dannert C. 2010b. Selectivity of Fungal Sesquiterpene Synthases: Role of the Active Site's H-I Loop in Catalysis. *Applied and Environmental Microbiology* 76: 7723-7733.

McCormick S P, Alexander N J, Harris U. 2010. CLM1 of Fusarium graminearum Encodes a Longiborneol Synthase Required for Culmorin Production. *Applied and Environmental Microbiology* 76: 136-141.

Medjahed F, Merouane A, Saadi A, Bader A, Cioni P L, Flamini G. 2016. Chemical profile and antifungal potential of essential oils from leaves and flowers of Salvia algeriensis (Desf.): A comparative study. *Chilean journal of agricultural research* 76: 195-200.

Menotta M. Gioacchini A M, Amicucci A, Buffalini M, Sisti D. Stocchi V. 2004. Headspace solid-phase microextraction with gas chromatography and mass spectrometry in the investigation of volatile organic compounds in an ectomycorrhizae synthesis system. *Rapid Communications in Mass Spectrometry* 18: 206-210.

Meshram V, Saxena S, Kapoor N. 2014. <I>Muscodor strobelii</I>, a new endophytic species from South India. *Mycotaxon* 128: 93-104.

Minerdi D, Bossi S, Gullino M L, Garibaldi A. 2009. Volatile organic compounds: A potential direct long-distance mechanism for antagonistic action of Fusarium oxysporum strain MSA 35. *Environmental Microbiology* 11: 844-854.

Molitor A, Zajic D, Voll L M, Pons-Kuhnemann J, Samans B, Kogel K-H, Waller F. 2011. Barley Leaf Transcriptome and Metabolite Analysis Reveals New Aspects of Compatibility and Piriformospora indica-Mediated Systemic Induced Resistance to Powdery Mildew. /1427 MPMI24: 1427-1439.

Morrone D, Lowry L, Determan M K, Hershey D M, Xu M, Peters R J. 2010. Increasing diterpene yield with a modular metabolic engineering system in E. coli: Comparison of MEV and MEP isoprenoid precursor pathway engineering. *Applied Microbiology and Biotechnology* 85: 1893-1906.

Padovan A, Keszei A, Kollner T G, Degenhardt J, Foley W J. 2010. The molecular basis of host plant selection in Melaleuca quinquenervia by a successful biological control agent. *Phytochemistry* 71: 1237-1244.

Pinedo C. Wang C-M, Pradier J-M, Dalmais B, Choquer M, Le Pecheur P. Morgant G, Collado I G, Cane D E, Viaud M. 2008. Sesquiterpene Synthase from the Botrydial Biosynthetic Gene Cluster of the Phytopathogen Botrytis cinerea. *ACS Chemical Biology* 3: 791-801.

Quin M B, Michel S N, Schmidt-Dannert C. 2015. Moonlighting Metals: Insights into Regulation of Cyclization Pathways in Fungal A6-Protoilludene Sesquiterpene Synthases. *ChemBioChem* 16: 2191-2199.

Ramirez J, Gilardoni G, Ram6n E. Tosi S, Picco A. Bicchi C, Vidari G. 2018. Phytochemical Study of the Ecuadorian Species Lepechinia mutica (Benth.) Epling and High Antifungal Activity of Carnosol against Pyricularia oryzae. *Pharmaceuticals* 11: 33.

Ray P, Chi M-H, Guo Y. Chen C, Adam C. Kuo A, LaButti K. Lipzen A, Barry K W, Grigoriev I V., et al. 2018. Genome Sequence of the Plant Growth Promoting Fungus Serendipita vermifera subsp. bescii: The First Native Strain from North America. *Phytobiomes Journal* 2: 62-63.

Scher J M, Speakman J-B, Zapp J, Becker H. 2004. Bioactivity guided isolation of antifungal compounds from the liverwort Bazzania trilobata (L.) S. F. Gray. *Phytochemistry* 65: 2583-2588.

Schmidt-Dannert C. 2014. Biosynthesis of Terpenoid Natural Products in Fungi. In: Advances in Biochemical Engineering/Biotechnology. 19-61.

Schmittgen T D, Livak K J. 2008. Analyzing real-time PCR data by the comparative C T method. *Nature Protocols* 3: 1101-1108.

Schüffler A. 2018. Secondary Metabolites of Basidiomycetes. In: Physiology and Genetics. Chain: Springer International Publishing, 231-275.

Shishova E Y, Di Costanzo L, Cane D E, Christianson D W. 2007. X-ray Crystal Structure of Aristolochene Synthase from *Aspergillus terreus* and Evolution of Templates for the Cyclization of Farnesyl Diphosphate †, ‡. *Biochemistry* 46: 1941-1951.

Trevizan L N F, Nascimento K F do, Santos J A, Kassuya C A L, Cardoso C A L, Vieira M do C, Moreira F M F, Croda J, Formagio A S N. 2016. Anti-inflammatory, antioxidant and anti-Mycobacterium tuberculosis activity of viridiflorol: The major constituent of Allophylus edulis (A. St.-Hil., A. Juss. & Cambess.) Radlk. *Journal of Ethnopharmacology* 192: 510-515.

Varma A, Verma S, Sudha †, Sahay N, Bu¨ tehornbu¨ bu¨ tehorn B, Franken P. 1999. *Piriformospora indica, a Cultivable Plant-Growth-Promoting Root Endophyte Downloaded from.*

Wang X Y, Joshi Y, Hur J. 2011. The genus. 117: 405-422.

Wawrzyn G T. Bloch S E, Schmidt-Dannert C. 2012a. Discovery and Characterization of Terpenoid Biosynthetic Pathways of Fungi. In: Methods in Enzymology. Elsevier Inc., 83-105.

Wawrzyn G T, Quin M B, Choudhary S, López-Gallego F, Schmidt-Dannert C. 2012b. Draft genome of omphalotus olearius provides a predictive framework for sesquiterpenoid natural product biosynthesis in basidiomycota. *Chemistry and Biology* 19: 772-783.

Weiss M, Selosse M A, Rexer K H, Urban A, Oberwinkler F. 2004. Sebacinales: A hitherto overlooked cosm of heterobasidiomycetes with a broad mycorrhizal potential. *Mycological Research*.

Wenke K, Kai M, Piechulla B. 2010. Belowground volatiles facilitate interactions between plant roots and soil organisms. *Planta* 231: 499-506.

Wu W. Tran W. Taatjes C A. Alonso-Gutierrez J, Lee T S, Gladden J M. 2016. Rapid Discovery and Functional Characterization of Terpene Synthases from Four Endophytic Xylariaceae (B Hamberger, Ed.). *PLOS ONE* 11: e0146983.

Xu L, Wang A, Wang J, Wei Q, Zhang W. 2017. Piriformospora indica confers drought tolerance on Zea mays L. through enhancement of antioxidant activity and expression of drought-related genes. *The Crop Journal* 5: 251-258.

Yuan X. 2005. Lichen-Like Symbiosis 600 Million Years Ago. *Science* 308: 1017-1020.

Zuccaro A, Lahrmann U, Guldener U, Langen G, Pfiffi S, Biedenkopf D, Wong P, Samans B. Grimm C, Basiewicz M, et al. 2011. Endophytic Life Strategies Decoded by Genome and Transcriptome Analyses of the Mutualistic Root Symbiont Piriformospora indica (BJ Howlett, Ed.). *PLoS Pathogens* 7: e1002290.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various features of the invention according to the foregoing description provided in the specification and figures.

Statements:

1. An expression system comprising at least one expression cassette having a heterologous promoter operably linked to a nucleic acid segment encoding an enzyme that catalyzes synthesis of viridiflorol.
2. An expression system comprising at least one expression cassette having a heterologous promoter operably linked to a nucleic acid segment encoding an enzyme with at least 90% sequence identity to SEQ ID NO:1, 3, 4, or 5.
3. The expression system of statement 1 or 2, wherein at least one expression cassette is within at least one expression vector.
4. The expression system of statement 1, 2 or 3, wherein the expression system further comprises one or more expression cassettes having a promoter operably linked to a nucleic acid segment encoding an enzyme that can synthesize isopentenyl diphosphate (IPP), dimethylallyl diphosphate (DMAPP), or geranylgeranyl diphosphate (GGPP).
5. The expression system of statement 1-3 or 4, wherein the expression system has at least one expression cassette having a constitutive promoter.
6. The expression system of statement 1-3 or 4, wherein the expression system has at least one expression cassette having an inducible promoter.
7. The expression system of statement 1-5 or 6, wherein the expression system has at least one expression cassette having the heterologous promoter is a lac promoter, a T7 promoter, a *Serendipita indica* FCGB1 promoter, CaMV 35S promoter, CaMV 19S promoter, nos promoter, Adh1 promoter, sucrose synthase promoter, α-tubulin promoter, ubiquitin promoter, actin promoter, cab promoter, PEPCase promoter, R gene complex promoter, CYP71D16 trichome-specific promoter, CBTS (cembratrienol synthase) promotor, Z10 promoter from a 10 kD zein protein gene, Z27 promoter from a 27 kD zein protein gene, plastid rRNA-operon (rrn) promoter, light inducible pea rbcS gene, RUBISCO-SSU light-inducible promoter (SSU) from tobacco, or rice actin promoter.
8. A host cell comprising the expression system of statement 1-6 or 7, which expression system is heterologous to the host cell.
9. The host cell of statement 8, which is a plant cell, an algae cell, a fungal cell, a bacterial cell, or an insect cell.

10. The host cell of statement 8 or 9, which is a fungal cell or a bacterial cell.

11. A method of synthesizing a terpene comprising incubating a host cell that has the expression system of any of statements 1-7.

12. A method for synthesizing a terpene comprising incubating a host cell comprising a heterologous expression system that includes at least one expression cassette having a heterologous promoter operably linked to a nucleic acid segment encoding an enzyme with at least 90% sequence identity to SEQ ID NO:1, 3, 4, or 5.

13. A method for synthesizing a terpene comprising incubating a terpene precursor with an enzyme with at least 90% sequence identity to SEQ ID NO: 1,3,4, or 5.

14. The method of statement 11, 12, or 13, further comprising isolating one or more terpenes.

15. The method of statement 11-13 or 14, wherein the terpene synthesized and/or isolated is viridiflorol.

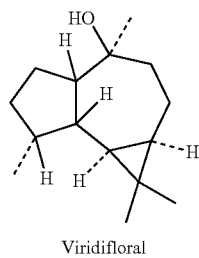

Viridifloral

16. A reaction mixture comprising one or more of the following:

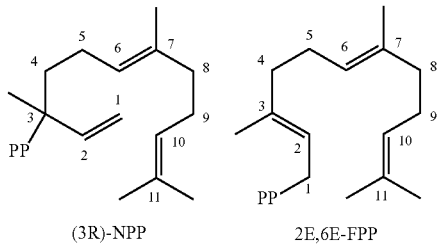

(3R)-NPP      2E,6E-FPP

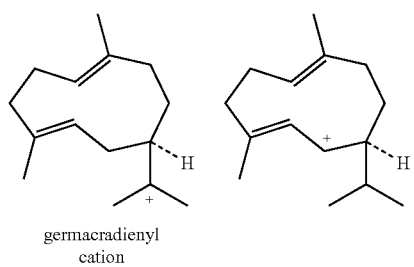

germacradienyl cation

-continued

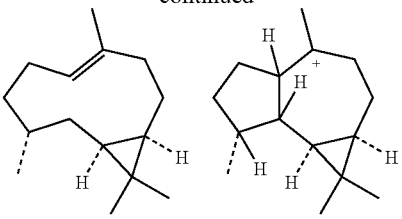

The specific methods, expression systems, and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. An expression system comprising at least one expression cassette having a heterologous promoter operably linked to a nucleic acid segment encoding a Serendipita indica terpenoid synthase (SiTPS) enzyme with at least 95% sequence identity to SEQ ID NO: 1, wherein the enzyme is capable of synthesizing viridiflorol.

2. The expression system of claim 1, wherein the heterologous promoter is a bacterial, plant, or fungal promoter.

3. The expression system of claim 1, wherein the heterologous promoter is a lac promoter, a T7 promoter, a Serendipita indica FCGB1 promoter, CaMV 35S promoter, CaMV 19S promoter, nos promoter, Adhl promoter, sucrose synthase promoter, a-tubulin promoter, ubiquitin promoter, actin promoter, cab promoter, PEPCase promoter, R gene complex promoter, CYP71D16 trichome-specific promoter, CBTS (cembratrienol synthase) promotor, Z10 promoter from a 10 kD zein protein gene, Z27 promoter from a 27 kD zein protein gene, plastid rRNA-operon (rrn) promoter, light inducible pea rbcS gene, RUBISCO-SSU light-inducible promoter (SSU) from tobacco, or rice actin promoter.

4. A host cell comprising the expression system of claim 1, which expression system is heterologous to the host cell.

5. The host cell of claim 4, which is a plant cell, an algae cell, a fungal cell, a bacterial cell, or an insect cell.

6. A method for synthesizing viridiflorol comprising incubating a host cell or a plant, wherein the host cell or the plant comprises a heterologous expression system that includes at least one expression cassette having a heterologous promoter operably linked to a nucleic acid segment encoding a Serendipita indica terpenoid synthase (SiTPS) enzyme with at least 95% sequence identity to SEQ ID NO:1.

7. A method for synthesizing viridiflorol comprising incubating a reaction mixture comprising a terpene precursor with a Serendipita indica terpenoid synthase (SiTPS) enzyme having at least 95% sequence identity to SEQ ID NO: 1, wherein the terpene precursor comprises E,E-FPP.

8. The method of claim 6, further comprising isolating viridiflorol from the host cell, the plant, or the reaction mixture.

9. The method of claim 7, further comprising isolating viridiflorol from the host cell, the plant, or the reaction mixture.

* * * * *

UNITED STATES PATENT AND TRADEMARK OFFICE
CERTIFICATE OF CORRECTION

PATENT NO. : 12,415,997 B2
APPLICATION NO. : 17/641802
DATED : September 16, 2025
INVENTOR(S) : Fani Ntana et al.

Page 1 of 1

It is certified that error appears in the above-identified patent and that said Letters Patent is hereby corrected as shown below:

In the Claims

In Claim 1, Column 57, Lines 48-49:
DELETE: "Serendipita indica terpenoid synthase (SiTPS)"
INSERT: --*Serendipita indica* terpenoid synthase(*Si*TPS)--

In Claim 3, Column 57, Line 56:
DELETE: "Serendipita indica"
INSERT: --*Serendipita indica*--

In Claim 3, Column 57, Line 57:
DELETE: "Adh1"
INSERT: --*Adh1*--

In Claim 3, Column 57, Line 59:
DELETE: "cab"
INSERT: --*cab*--

In Claim 6, Column 58, Line 53:
DELETE: "Serendipita indica terpenoid synthase (SiTPS)"
INSERT: --*Serendipita indica* terpenoid synthase(*Si*TPS)--

In Claim 7, Column 58, Line 57:
DELETE: "Serendipita indica terpenoid synthase (SiTPS)"
INSERT: --*Serendipita indica* terpenoid synthase(*Si*TPS)--

In Claim 7, Column 58, Line 59:
DELETE: "E,E-FPP"
INSERT: --*E,E*-FPP--

Signed and Sealed this
Ninth Day of December, 2025

John A. Squires
*Director of the United States Patent and Trademark Office*

SEQUENCE LISTING

<160> NUMBER OF SEQ ID NOS: 26

<210> SEQ ID NO 1
<211> LENGTH: 523
<212> TYPE: PRT
<213> ORGANISM: Serendipita indica

<400> SEQUENCE: 1

```
Met Pro Ser Val Ser Pro Ala Thr Ile Arg Leu Pro Asp Ile Leu Gly
1               5                   10                  15

Ala Met Asp Arg Phe Glu Leu Arg Thr His Pro Asp Glu Arg Glu Val
            20                  25                  30

Thr Arg Ala Ser Asn Glu Trp Phe Asn Ser Tyr Asn Met Met Pro Pro
        35                  40                  45

Ala Leu Phe Glu Lys Phe Val Lys Cys Asp Phe Gly Leu Met Thr Gly
    50                  55                  60

Met Ser Tyr Pro Asp Thr Asp Ala Thr Arg Leu Arg Ile Thr Cys Asp
65                  70                  75                  80

Tyr Met Ser Ile Leu Phe Ala Tyr Asp Asp Leu Met Asp Leu Pro Ser
                85                  90                  95

Ser Asp Leu Met His Asp Lys Ile Ala Ser Asp Lys Ala Ala Lys Ile
            100                 105                 110

Met Met Gly Val Leu Thr His Pro His Lys Phe Arg Pro Tyr Ala Gly
        115                 120                 125

Leu Pro Val Ala Thr Ala Phe His Asp Phe Trp Thr Arg Phe Cys Ala
130                 135                 140

Thr Ser Thr Pro Lys Met Gln Lys Arg Phe Thr Asp Thr Thr Tyr Glu
145                 150                 155                 160

Tyr Val Met Ala Val Lys Asn Gln Cys Gly Asn Arg Gln Ser Ser Arg
                165                 170                 175

Cys Pro Thr Ile Glu Glu Tyr Val Ala Leu Arg Arg Asp Thr Ser Ala
            180                 185                 190

Ile Lys Val Thr Tyr Ala Cys Ile Glu Tyr Cys Leu Asn Ile Asp Val
        195                 200                 205

Pro Asp Glu Ala Phe Tyr His Pro Ser Val Ala Ala Leu Gln Glu Ala
    210                 215                 220

Gly Asn Asn Ile Leu Ser Trp Ala Asn Asp Val Tyr Ser Phe Asp Asn
225                 230                 235                 240

Glu Gln Ser Ser Gly Asp Cys His Asn Leu Val Ala Ile Val Ala Ile
                245                 250                 255

Asn Lys Asn Ile Thr Val Gln Ala Ala Met Glu Tyr Val Met Gly Met
            260                 265                 270

Ile Asp Ser Ala Ile Glu Arg Phe Phe Glu Glu Cys Ala Asn Val Pro
        275                 280                 285

Ser Phe Gly Pro Glu Val Asp Pro Leu Val Gln Ala Tyr Ile Lys Gly
    290                 295                 300

Val Glu Leu Tyr Leu Ser Gly Ser Val Phe Trp His Leu Glu Ser Glu
305                 310                 315                 320

Arg Tyr Phe Gly Ala Arg Val Gln His Val Lys Asp Thr Leu Met Val
                325                 330                 335

Glu Leu Arg Pro Leu Asp Glu Gly Ala Lys Pro Ala Phe Asp Leu Met
            340                 345                 350

Tyr Lys Leu Pro Ser Asn Leu Thr Pro Glu Val Leu Ser Ala Ala Ala
        355                 360                 365
```

Val Ser Ala Ala Pro Ala Pro Ala Pro Val Ala Ser Pro Ala Pro
    370             375             380
Gln Pro Glu Ile Leu Ser Pro Thr Pro Ile Ser Pro Ile Asn Val Asn
385             390             395             400
Phe Pro Leu Gly Asn Val Ala Cys Pro Pro Ser Tyr Glu Thr Gln
            405             410             415
Arg Val Leu Ala Lys Met Val Ala Ala Thr Val Glu Glu Lys Gln Arg
            420             425             430
Leu Ala Tyr Ser Gln Pro Ala Glu Gln Tyr Tyr Ser Pro Ala Pro Gln
        435             440             445
Tyr Tyr Pro Ser Gln Pro Val Glu Lys Phe Gln Gln Thr Asn Val Leu
450             455             460
Glu Thr Ala Phe Lys Gly Ser Asn Ser Glu Leu Thr Asn Ile Leu Val
465             470             475             480
Ile Ala Ser Val Leu Met Ala Gly Ser Pro Met Ala Leu Val Pro Phe
                485             490             495
Val Pro Leu Leu Ala Leu Leu Leu Pro Asn Glu Thr Pro Val Ala
            500             505             510
Pro Val Ala Phe Glu His His His His His His
            515             520

<210> SEQ ID NO 2
<211> LENGTH: 1569
<212> TYPE: DNA
<213> ORGANISM: Serendipita indica

<400> SEQUENCE: 2

```
atgccatctg tctctcctgc caccatccgc ctccctgata tcctcggtgc tatggaccgc      60
tttgagctcc gcactcaccc cgatgagcgc gaagtcaccc gtgcctcgaa cgagtggttc     120
aacagctaca acatgatgcc cccggcactc tttgaaaagt tgtcaagtg cgatttcggc      180
ctcatgaccg gcatgtcgta cccagatacc gatgctaccc gctccgtat cacttgcgac      240
tacatgtcga tcctcttcgc ctatgacgac ctcatggacc tcccctcgtc cgaccttatg     300
catgacaaga ttgcctcgga caaggctgcc aagatcatga tgggtgtcct cacccacccc     360
cacaagttcc gcccatatgc tggcctccca gtcgccactg ctttccatga cttctggacc     420
cgcttctgcg ctacttcgac cccaaagatg caaaagcgct tcactgacac cacctacgag     480
tatgtcatgg ccgtcaagaa ccagtgcggc aaccgccaga gctctcgctg cccaaccatc     540
gaggagtacg tcgctctccg ccgcgacacc tcggccatca ggtcaccta tgcttgcatc     600
gagtactgcc tcaacatcga cgtcccagac gaggccttct accacccctc cgtggctgct     660
ctccaggagg ctggcaataa tatcctctcg tgggccaacg atgtttactc gtttgacaac     720
gagcaatcct cgggtgactg ccacaacctc gttgccattg ttgccatcaa caagaacatt     780
actgttcagg ctgcaatgga gtacgtcatg gcatgatcg actctgctat cgaacgcttc     840
ttcgaggagt gcgccaacgt cccttcgttc ggccccgaag tcgacccctct cgtccaggcc     900
tacatcaagg gtgtcgagct ctaccttagc ggctccgtct tctggcacct cgaatccgag     960
cgctactttg tgctcgcgt ccagcacgtc aaggatacct tgatggttga gctccgccca    1020
ctcgacgagg gtgcgaagcc ggccttcgac ctcatgtaca agctcccatc caacttgacg    1080
cccgaggtcc tcagtgccgc tgctgtctcg gctgccccag ctgcgccagc tcctgtcgct    1140
tctccggctc ctcagccaga gatcctctcg ccgacgccaa tctcgcccat caacgtcaac    1200
ttccctctcg gcaacgtcgc ctgcccgcct ccttcgtacg agacccagcg cgttctcgcc    1260
```

```
aagatggtgg ccgcgaccgt cgaggagaag cagcgccttg cttacagcca gccagctgag    1320
cagtactact cgcccgctcc ccagtactac ccaagccagc cggttgaaaa gttccagcag    1380
accaacgtgc tcgagaccgc cttcaaggga tccaactcgg aattgaccaa cattctcgtt    1440
attgcctccg tcctcatggc cggatcaccc atggcgcttg tccccttttgt ccctcttctc   1500 gccctcctac tcctccccaa cgagacccca gtggctcccg ttgcgttcga gcaccaccac    1560
caccaccac                                                            1569
```

<210> SEQ ID NO 3
<211> LENGTH: 517
<212> TYPE: PRT
<213> ORGANISM: Serendipita indica

<400> SEQUENCE: 3

```
Met Pro Ser Val Ser Pro Ala Thr Ile Arg Leu Pro Asp Ile Leu Gly
1               5                   10                  15

Ala Met Asp Arg Phe Glu Leu Arg Thr His Pro Asp Glu Arg Glu Val
            20                  25                  30

Thr Arg Ala Ser Asn Glu Trp Phe Asn Ser Tyr Asn Met Met Pro Pro
        35                  40                  45

Ala Leu Phe Glu Lys Phe Val Lys Cys Asp Phe Gly Leu Met Thr Gly
    50                  55                  60

Met Ser Tyr Pro Asp Thr Asp Ala Thr Arg Leu Arg Ile Thr Cys Asp
65                  70                  75                  80

Tyr Met Ser Ile Leu Phe Ala Tyr Asp Asp Leu Met Asp Leu Pro Ser
                85                  90                  95

Ser Asp Leu Met His Asp Lys Ile Ala Ser Asp Lys Ala Ala Lys Ile
            100                 105                 110

Met Met Gly Val Leu Thr His Pro His Lys Phe Arg Pro Tyr Ala Gly
        115                 120                 125

Leu Pro Val Ala Thr Ala Phe His Asp Phe Trp Thr Arg Phe Cys Ala
    130                 135                 140

Thr Ser Thr Pro Lys Met Gln Lys Arg Phe Thr Asp Thr Thr Tyr Glu
145                 150                 155                 160

Tyr Val Met Ala Val Lys Asn Gln Cys Gly Asn Arg Gln Ser Ser Arg
                165                 170                 175

Cys Pro Thr Ile Glu Glu Tyr Val Ala Leu Arg Arg Asp Thr Ser Ala
            180                 185                 190

Ile Lys Val Thr Tyr Ala Cys Ile Glu Tyr Cys Leu Asn Ile Asp Val
        195                 200                 205

Pro Asp Glu Ala Phe Tyr His Pro Ser Val Ala Ala Leu Gln Glu Ala
    210                 215                 220

Gly Asn Asn Ile Leu Ser Trp Ala Asn Asp Val Tyr Ser Phe Asp Asn
225                 230                 235                 240

Glu Gln Ser Ser Gly Asp Cys His Asn Leu Val Ala Ile Val Ala Ile
                245                 250                 255

Asn Lys Asn Ile Thr Val Gln Ala Ala Met Glu Tyr Val Met Gly Met
            260                 265                 270

Ile Asp Ser Ala Ile Glu Arg Phe Phe Glu Glu Cys Ala Asn Val Pro
        275                 280                 285

Ser Phe Gly Pro Glu Val Asp Pro Leu Val Gln Ala Tyr Ile Lys Gly
    290                 295                 300

Val Glu Leu Tyr Leu Ser Gly Ser Val Phe Trp His Leu Glu Ser Glu
```

-continued

```
                305                 310                 315                 320
        Arg Tyr Phe Gly Ala Arg Val Gln His Val Lys Asp Thr Leu Met Val
                        325                 330                 335

Glu Leu Arg Pro Leu Asp Glu Gly Ala Lys Pro Ala Phe Asp Leu Met
                        340                 345                 350

Tyr Lys Leu Pro Ser Asn Leu Thr Pro Glu Val Leu Ser Ala Ala Ala
                        355                 360                 365

Val Ser Ala Ala Pro Ala Ala Pro Ala Pro Val Ala Ser Pro Ala Pro
                        370                 375                 380

Gln Pro Glu Ile Leu Ser Pro Thr Pro Ile Ser Pro Ile Asn Val Asn
        385                 390                 395                 400

Phe Pro Leu Gly Asn Val Ala Cys Pro Pro Ser Tyr Glu Thr Gln
                        405                 410                 415

Arg Val Leu Ala Lys Met Val Ala Thr Val Glu Glu Lys Gln Arg
                        420                 425                 430

Leu Ala Tyr Ser Gln Pro Ala Glu Gln Tyr Tyr Ser Pro Ala Pro Gln
                        435                 440                 445

Tyr Tyr Pro Ser Gln Pro Val Glu Lys Phe Gln Gln Thr Asn Val Leu
                        450                 455                 460

Glu Thr Ala Phe Lys Gly Ser Asn Ser Glu Leu Thr Asn Ile Leu Val
        465                 470                 475                 480

Ile Ala Ser Val Leu Met Ala Gly Ser Pro Met Ala Leu Val Pro Phe
                        485                 490                 495

Val Pro Leu Leu Ala Leu Leu Leu Pro Asn Glu Thr Pro Val Ala
                        500                 505                 510

Pro Val Ala Phe Glu
                        515

<210> SEQ ID NO 4
<211> LENGTH: 522
<212> TYPE: PRT
<213> ORGANISM: Serendipita indica

<400> SEQUENCE: 4

Met Pro Ser Val Ser Pro Ala Thr Ile Arg Leu Pro Asp Ile Leu Gly
        1               5                   10                  15

Ala Met Asp Arg Phe Glu Leu Arg Thr His Pro Asp Glu Arg Glu Val
                        20                  25                  30

Thr Arg Ala Ser Asn Glu Trp Phe Asn Ser Tyr Asn Met Met Pro Pro
                        35                  40                  45

Ala Leu Phe Glu Lys Phe Val Lys Cys Asp Phe Gly Leu Met Thr Gly
                        50                  55                  60

Met Ser Tyr Pro Asp Thr Asp Ala Thr Arg Leu Arg Ile Thr Cys Asp
        65                  70                  75                  80

Tyr Met Ser Ile Leu Phe Ala Tyr Asp Asp Leu Met Asp Leu Pro Ser
                        85                  90                  95

Ser Asp Leu Met His Asp Lys Ile Ala Ser Asp Lys Ala Ala Lys Ile
                        100                 105                 110

Met Met Gly Val Leu Thr His Pro His Lys Phe Arg Pro Tyr Ala Gly
                        115                 120                 125

Leu Pro Val Ala Thr Ala Phe His Asp Phe Trp Thr Arg Phe Cys Ala
                        130                 135                 140

Thr Ser Thr Pro Lys Met Gln Lys Arg Phe Thr Asp Thr Thr Tyr Glu
        145                 150                 155                 160
```

```
Tyr Val Met Ala Val Lys Asn Gln Cys Gly Asn Arg Gln Ser Ser Arg
                165                 170                 175

Cys Pro Thr Ile Glu Glu Tyr Val Ala Leu Arg Arg Asp Thr Ser Ala
            180                 185                 190

Ile Lys Val Thr Tyr Ala Cys Ile Glu Tyr Cys Leu Asn Ile Asp Val
        195                 200                 205

Pro Asp Glu Ala Phe Tyr His Pro Ser Val Ala Leu Gln Glu Ala
    210                 215                 220

Gly Asn Ile Leu Ser Trp Ala Asn Asp Val Tyr Ser Phe Asp Asn Glu
225                 230                 235                 240

Gln Ser Ser Gly Asp Cys His Asn Leu Val Ala Ile Ala Ile Asn
                245                 250                 255

Lys Asn Ile Thr Val Gln Ala Ala Met Glu Tyr Val Met Gly Met Ile
            260                 265                 270

Asp Ser Ala Ile Glu Arg Phe Phe Glu Glu Cys Ala Asn Val Pro Ser
        275                 280                 285

Phe Gly Pro Glu Val Asp Pro Leu Val Gln Ala Tyr Ile Lys Gly Val
    290                 295                 300

Glu Leu Tyr Leu Ser Gly Ser Val Phe Trp His Leu Glu Ser Glu Arg
305                 310                 315                 320

Tyr Phe Gly Ala Arg Val Gln His Val Lys Asp Thr Leu Met Val Glu
                325                 330                 335

Leu Arg Pro Leu Asp Glu Gly Ala Lys Pro Ala Phe Asp Leu Met Tyr
            340                 345                 350

Lys Leu Pro Ser Asn Leu Thr Pro Glu Val Leu Ser Ala Ala Ala Val
        355                 360                 365

Ser Ala Ala Pro Ala Ala Pro Ala Pro Val Ala Ser Pro Ala Pro Gln
    370                 375                 380

Pro Glu Ile Leu Ser Pro Thr Pro Ile Ser Pro Ile Asn Val Asn Phe
385                 390                 395                 400

Pro Leu Gly Asn Val Ala Cys Pro Pro Ser Tyr Glu Thr Gln Arg
                405                 410                 415

Val Leu Ala Lys Met Val Ala Ala Thr Val Glu Glu Lys Gln Arg Leu
            420                 425                 430

Ala Tyr Ser Gln Pro Ala Glu Gln Tyr Tyr Ser Pro Ala Pro Gln Tyr
        435                 440                 445

Tyr Pro Ser Gln Pro Val Glu Lys Phe Gln Gln Thr Asn Val Leu Glu
    450                 455                 460

Thr Ala Phe Lys Gly Ser Asn Ser Glu Leu Thr Asn Ile Leu Val Ile
465                 470                 475                 480

Ala Ser Val Leu Met Ala Gly Ser Pro Met Ala Leu Val Pro Phe Val
                485                 490                 495

Pro Leu Leu Ala Leu Leu Leu Pro Asn Glu Thr Pro Val Ala Pro
            500                 505                 510

Val Ala Phe Glu His His His His His His
        515                 520

<210> SEQ ID NO 5
<211> LENGTH: 295
<212> TYPE: PRT
<213> ORGANISM: Cladonia uncialis

<400> SEQUENCE: 5

Met Cys Ala Glu Trp Ile Thr Val Leu Phe Val Trp Asp Asp Leu Leu
1               5                   10                  15
```

```
Asp Val Pro Ile Asp Ser Asp Leu Val Ser Asp Glu Gln Gly Thr Arg
         20                  25                  30

Glu Ile Asn Arg Val Met Ser Cys Ile Leu Thr Gln Pro Glu Asn Phe
             35                  40                  45

Glu Pro Met Val Thr Gln Pro Val Thr Gly Ala Leu His Ser Phe Trp
         50                  55                  60

Thr Gln Phe Cys Ala Thr Ser Ser Pro Asn Met Gln Lys Arg Phe Val
 65                  70                  75                  80

Glu Ala Val Leu Lys Tyr Ala Glu Gly Ala Lys Gln Val Ala Ser
                 85                  90                  95

Arg Glu Thr Arg Ala Leu Pro Ser Ile Lys Asp Phe Ile Val Asn Arg
                100                 105                 110

Gln Ser Ala Ser Gly Val Glu Thr Leu Leu Ala Leu Val Glu Tyr Cys
            115                 120                 125

Leu Gln Ile Gln Val Pro Asp Cys Ala Tyr Tyr His Pro Thr Leu Gln
130                 135                 140

Gln Leu Arg Asn Ser Ile Asn Glu Ile Val Ser Trp Ser Asn Asp Ile
145                 150                 155                 160

Tyr Ser Phe Asn Lys Glu Gln Ala Cys Gly Asp His Ala Asn Leu Val
                165                 170                 175

Val Val Val Ala Ile Glu Lys Gly Ile Pro Val Gln Ser Ala Ile Thr
            180                 185                 190

Tyr Val Ser Val Met Val Gln Glu Ala Val Lys Arg Tyr His Glu Asn
        195                 200                 205

Leu Lys Lys Ile Pro Lys Phe Asp Pro Arg Ile Asp Ala Leu Val Leu
210                 215                 220

Lys Tyr Val Gly Gly Ile Glu Cys Val Cys Thr Gly Leu Val Ser Trp
225                 230                 235                 240

His Phe Lys Ile Asp Arg Tyr Phe Gly Glu Asn Ser Ser Glu Val Ser
                245                 250                 255

Asn Thr Leu Met Val Asp Leu Leu Pro Gln Glu Lys Asn Ala Leu Val
            260                 265                 270

Ser Ala His Glu Leu Gln Tyr Asp Gln Leu Pro Ile Ser Thr Pro Gln
        275                 280                 285

Pro Lys Gly Ser Ala Met Thr
    290                 295

<210> SEQ ID NO 6
<211> LENGTH: 6
<212> TYPE: PRT
<213> ORGANISM: Artificial Sequence
<220> FEATURE:
<223> OTHER INFORMATION: A synthetic polypeptide

<400> SEQUENCE: 6

His His His His His His
1               5

<210> SEQ ID NO 7

<400> SEQUENCE: 7

000

<210> SEQ ID NO 8

<400> SEQUENCE: 8
```

000

<210> SEQ ID NO 9
<400> SEQUENCE: 9

000

<210> SEQ ID NO 10
<400> SEQUENCE: 10

000

<210> SEQ ID NO 11
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 11
agaaggagat ataccatgcc atctgtctct cctgccac                          38

<210> SEQ ID NO 12
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 12
ggtggtggtg ctcgaacgca acgggagcca ctggg                             35

<210> SEQ ID NO 13
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 13
ctccaaaaac agtcgatgcc atctgtctct cctgc                             35

<210> SEQ ID NO 14
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 14
tagatatcgt agtttgcaac gggagccact ggggt                             35

<210> SEQ ID NO 15
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 15
cgatacctac ccgcctacaa                                              20

<210> SEQ ID NO 16

```
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16 cttttttaagc ggtgctggag                                              20

<210> SEQ ID NO 17
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 17
atgagtacga ttgcccaagg                                               20

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 18
tcgtctcgta ggcgactttt                                               20

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
agatatccgg aggcgagttt                                               20

<210> SEQ ID NO 20
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 20
cctgaatctg ctgttcgtca                                               20

<210> SEQ ID NO 21
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 21
acatctggct cccatttacg                                               20

<210> SEQ ID NO 22
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 22
```

```
gttgagcttt ggctcgtttc                                                    20

<210> SEQ ID NO 23
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 23
caacacatgt gcacgtcgat                                                    20

<210> SEQ ID NO 24
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 24
ccaatgtgca ttcagaacga                                                    20

<210> SEQ ID NO 25
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 25
aacctccatt caggagatgt tt                                                 22

<210> SEQ ID NO 26
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 26
tgctgtagca tcctggtatt                                                    20
```